United States Patent
Wu

(10) Patent No.: US 8,962,626 B2
(45) Date of Patent: *Feb. 24, 2015

(54) THIENOPYRIDAZINE COMPOUNDS, THEIR PREPARATIONS, PHARMACEUTICAL COMPOSITIONS AND USES

(75) Inventor: Zhanggui Wu, Hangzhou (CN)

(73) Assignee: Zhejiang Medicine Co., Ltd. Xinchang Pharmaceutical Factory, Xinchang County, Zhejiang Province (CN)

( * ) Notice: Subject to any disclaimer, the term of this patent is extended or adjusted under 35 U.S.C. 154(b) by 740 days.

This patent is subject to a terminal disclaimer.

(21) Appl. No.: 12/811,898

(22) PCT Filed: Jan. 7, 2009

(86) PCT No.: PCT/CN2009/000021
§ 371 (c)(1),
(2), (4) Date: Sep. 16, 2010

(87) PCT Pub. No.: WO2009/092278
PCT Pub. Date: Jul. 30, 2009

(65) Prior Publication Data
US 2011/0009415 A1    Jan. 13, 2011

(30) Foreign Application Priority Data

Jan. 8, 2008 (CN) ............ 2008 1 0000936
Jan. 6, 2009 (CN) ............ 2009 1 0000337

(51) Int. Cl.
| | | |
|---|---|---|
| *A01N 43/58* | (2006.01) | |
| *A01N 43/60* | (2006.01) | |
| *A61K 31/50* | (2006.01) | |
| *A61K 31/495* | (2006.01) | |
| *C07D 237/26* | (2006.01) | |
| *C07D 487/00* | (2006.01) | |
| *C07D 237/28* | (2006.01) | |
| *C07D 495/04* | (2006.01) | |

(52) U.S. Cl.
CPC ............... *C07D 495/04* (2013.01)
USPC ........................... 514/248; 544/235

(58) Field of Classification Search
USPC ........................... 514/248; 544/235
See application file for complete search history.

(56) References Cited

FOREIGN PATENT DOCUMENTS

WO    WO 2007124181 A2 * 11/2007

* cited by examiner

*Primary Examiner* — Samira Jean-Louis
(74) *Attorney, Agent, or Firm* — Ash Tankha; Lipton, Weinberger & Husick

(57) ABSTRACT

The present invention relates to thienopyridazine compounds of formula (I), their pharmaceutically acceptable salts or hydrates, wherein R1 and R2 are independently H or C1-4 alkyl, R3 is a saturated or unsaturated 5- or 6-membered ring containing N, S or O, or its optical isomers, R4 is a halophenyl monosubstituted or disubstituted at any position. The present invention provides the preparation methods of these compounds, pharmaceutical compositions containing these compounds and the uses of these compounds, particularly in treating cancer.

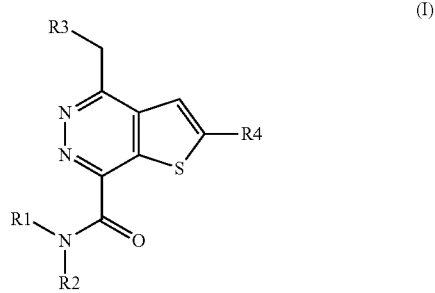

(I)

7 Claims, No Drawings

THIENOPYRIDAZINE COMPOUNDS, THEIR PREPARATIONS, PHARMACEUTICAL COMPOSITIONS AND USES

CROSS REFERENCE TO RELATED APPLICATIONS

This application claims the benefit of the following patent applications:
1. Chinese patent application number 200810000936.9 titled "Thienopyridazine Compounds, Their Preparations, Pharmaceutical Compositions And Uses", filed on 8 Jan. 2008 in the State Intellectual Property Office of the People's Republic Of China.
2. Chinese patent application number 200910000337.1 titled "Thienopyridazine Compounds, Their Preparations, Pharmaceutical Compositions And Uses", filed on 6 Jan. 2009 in the State Intellectual Property Office of the People's Republic Of China.
3. PCT application number PCT/CN2009/000021 titled "Thienopyridazine Compounds, Their Preparations, Pharmaceutical Compositions And Uses", filed on 7 Jan. 2009 in the State Intellectual Property Office of the People's Republic Of China.

The specifications of the above referenced applications are incorporated herein by reference in their entirety.

FIELD OF THE INVENTION

The present invention relates to pharmaceutical chemistry, in particular, relates to thienopyridazine compounds, their preparations, and pharmaceutical compositions containing them and uses thereof.

BACKGROUND OF THE INVENTION

Cancer is a major threat to human health, and a majority of cancers in human are caused by external environmental factors. Every year at least 5 million persons died of cancer around the world. The cure rate is still low although some treatment methods of cancers are currently available to cure patients, such as surgery, radiotherapy, chemotherapy and so on. Using chemical pharmaceuticals for preventing and treating cancers is currently one of the most effective methods.

Thienopyridazine compounds or compounds of their thieno analogues have been found to have anti-tumor activities.

F. Hoffman-La Roche AG discloses a thienopyridazine as an IKK inhibitor in WO2005105808.

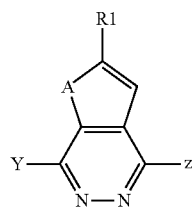

Amgen Inc. of USA discloses a thienopyridazine compound as a p38 protease inhibitor of tyrosine kinase in WO2007124181.

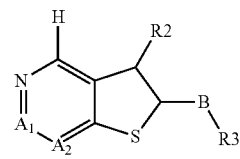

Smithkline Beecham Corporation discloses a 2-ureidothiophene compound in WO03029241 and a 3-ureidothiophene compound in WO03028731, which are similar to thienopyridazine compounds as CHK1 inhibitors. AstraZeneca AB discloses a 3-ureidothiophene modified compound as a CHK1 inhibitor in WO 2005066163.

Chemical pharmaceuticals for preventing and treating cancers currently include inhibitors of receptors of tyrosine kinases and non-receptors of tyrosine kinases, and their targets include VEGFR, EGFR, HER2, SRC, JAK and TEK; and also include inhibitors of threonine-serine kinases and their targets include MEK, JNK, c-MET, AKT, PIM, TIE, PLK and so on. The compounds of the present invention are inhibitors of cancers and protein kinases including Checkpoint Kinase CHK1/CHK2 of cell cycles.

It has been found from researches for regulations of checkpoints of cell cycle that closing expression of CHK1 can reverse drug resistance of cancer cells, thereby increase sensitivities of tumor cells to DNA damage therapy, and dramatically increase activities of anti-cancer pharmaceuticals. In addition, it may obtain tumors selective pharmaceuticals through majorities of tumors having mutations features in p53 of eliminating G1/S checkpoint. The present invention provides a novel thienopyridazine compound as inhibitors of protein kinases of novel tumors associated with growth factors (including CHK1, CHK2), which not only have anti-tumor actions but also can enhance anti-tumor effectiveness of other anti-tumor pharmaceuticals.

SUMMARY OF THE INVENTION

According to the present invention, the applicant found novel compounds having anti-proliferative activities (e.g. anti-cancer activities), and thereby used for treatment of human and animal. The present invention also relates to methods for preparation of said compounds, pharmaceutical compositions comprising them, and their uses in the preparation of pharmaceuticals for use in the production of anti-proliferative effects in worm-blooded animals such as human.

The present invention includes pharmaceutically acceptable salts or prodrugs of such compounds, and the applicant also provides pharmaceutical compositions and methods of using such compounds for treatment of cancer according to the present invention.

Such properties of compounds of the present invention are expected to be of useful values for treatments of diseases associated with cell cycle stagnation and cell proliferation as follows: cancer (solid tumor and leukemia), fibroproliferative and differentiative diseases, psoriasis, rheumatoid arthritis, Kaposi's sarcoma, acute and chronic nephropathies, atheroma, atherosclerosis, arterial restenosis, autoimmune diseases, acute and chronic inflammation, bone diseases and ocular diseases with retinal vessel proliferation.

According to one aspect of the present invention, the compounds of formula (I) or their pharmaceutically acceptable salts or hydrates are provided,

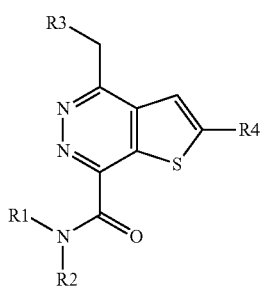

Wherein, R1 and R2 are independently H or $C_{1-4}$ alkyl;

R3 is a saturated or unsaturated 5- or 6-membered ring containing N, S or O, and optical isomers thereof;

R4 is a halophenyl mono substituted or disubstituted at any position.

Preferably, R1=R2=H.

Preferably, R3 is a saturated 6-membered ring containing N, S or O, and its optical isomers.

Preferably, R3 is hexahydropyridyl, tetrahydropyranyl, tetrahydrothiopyranyl, tetrahydropyrrolidinyl, tetrahydrofuranyl, or tetrahydrothienyl, and its optical isomers.

Preferably, R3 is hexahydropyridinyl, and its optical isomers.

Preferably, R4 is a monosubstituted halophenyl.

Preferably, R4 is

wherein, X represents F, Cl, Br, I.

More preferably, the compounds of formula (I) are selected from as follows:

2-(4-fluorophenyl)-4-(3-piperidinemethyl)-thieno[2,3-d]pyridazinyl-7-formamide;

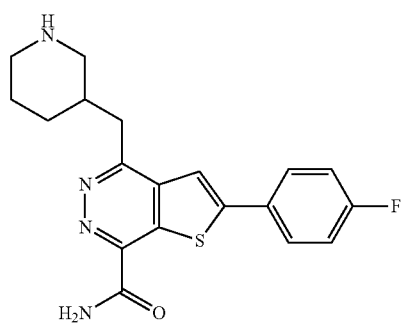

2-(4-chlorophenyl)-4-(3-piperidinemethyl)-thieno[2,3-d]pyridazinyl-7-formamide;

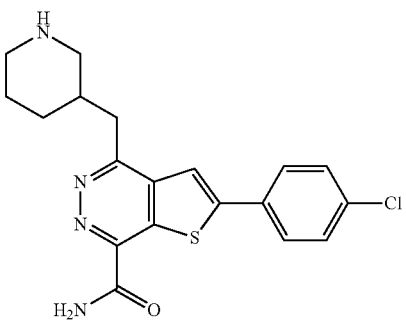

2-(4-bromophenyl)-4-(3-piperidinemethyl)-thieno[2,3-d]pyridazinyl-7-formamide;

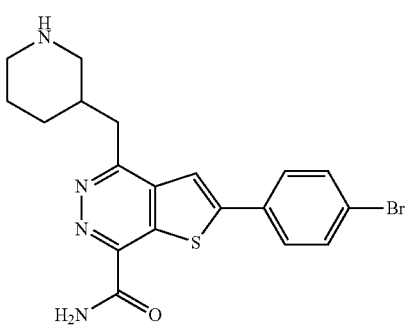

2-(4-fluorophenyl)-4-(3-tetrahydropyranmethyl)-thieno[2,3-d]pyridazinyl-7-formamide;

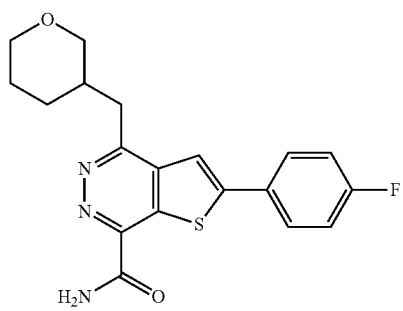

2-(4-chlorophenyl)-4-(3-tetrahydropyranmethyl)-thieno[2,3-d]pyridazinyl-7-formamide;

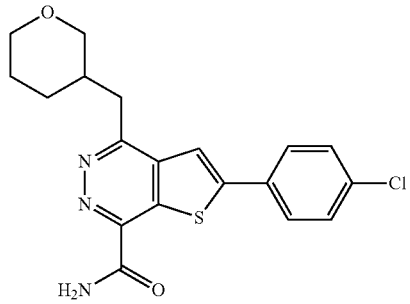

2-(4-bromophenyl)-4-(3-tetrahydropyranmethyl)-thieno[2,3-d]pyridazinyl-7-formamide;

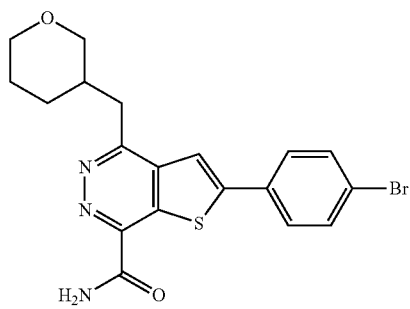

VI 2-(4-fluorophenyl)-4-(3-tetrahydrothiapyranmethyl)-thieno[2,3-d]pyridazinyl-7-formamide;

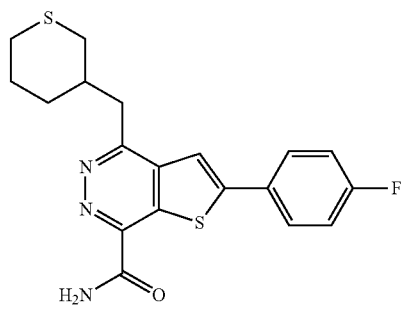

VII 2-(4-chlorophenyl)-4-(3-tetrahydrothiapyranmethyl)-thieno[2,3-d]pyridazinyl-7-formamide;

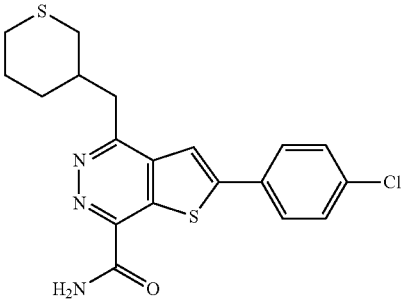

VIII 2-(4-bromophenyl)-4-(3-tetrahydrothiapyranmethyl)-thieno[2,3-d]pyridazinyl-7-formamide;

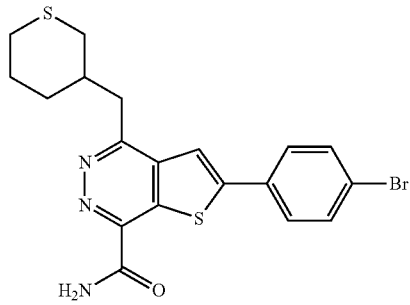

IX 2-(4-chlorophenyl)-4-(2-piperidinemethyl)-thieno[2,3-d]pyridazinyl-7-formamide;

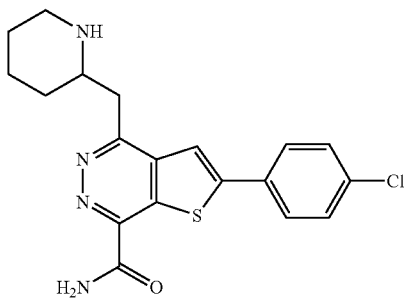

X 2-(4-chlorophenyl)-4-(4-piperidinemethyl)-thieno[2,3-d]pyridazinyl-7-formamide;

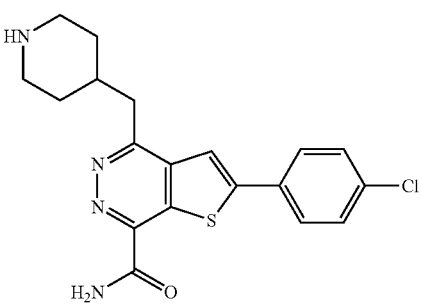

XI 2-(4-chlorophenyl)-4-(S-3-piperidinemethyl)-thieno[2,3-d]pyridazinyl-7-formamide;

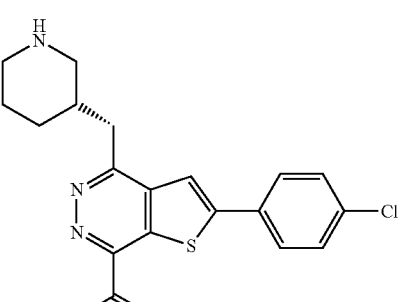

XII 2-(4-chlorophenyl)-4-(R-3-piperidinemethyl)-thieno[2,3-d]pyridazinyl-7-formamide;

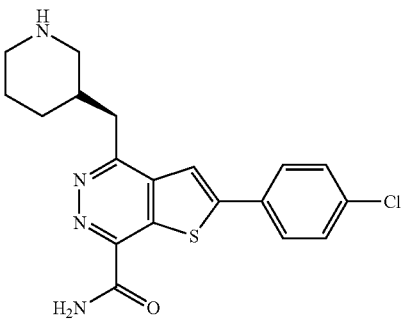

XIII 2-(4-chlorophenyl)-4-(3-piperidinemethyl)-thieno[2,3-d]pyridazinyl-7-N-methyl formamide;

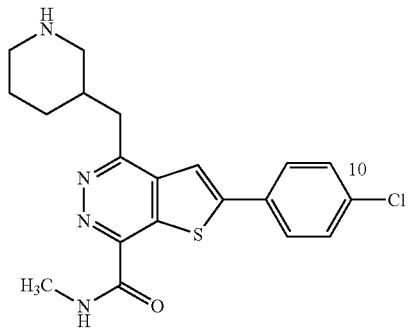

2-(4-chlorophenyl)-4-(3-piperidinemethyl)-thieno[2,3-d]pyridazinyl-7-N,N-dimethyl formamide;

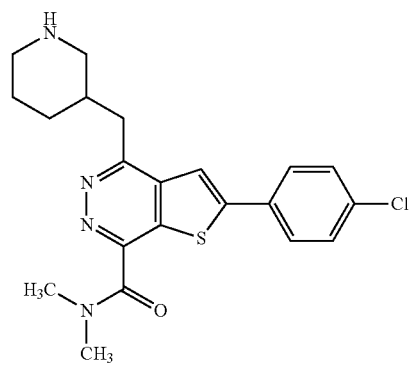

2-(4-chlorophenyl)-4-(3-tetrahydrothiapyranmethyl)-thieno[2,3-d]pyridazinyl-7-N-methyl formamide;

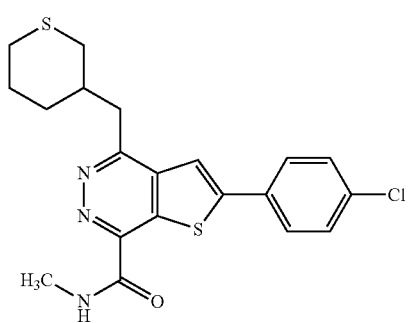

2-(4-chlorophenyl)-4-(3-tetrahydrothiapyranmethyl)-thieno[2,3-d]pyridazinyl-7-N,N-dimethyl formamide;

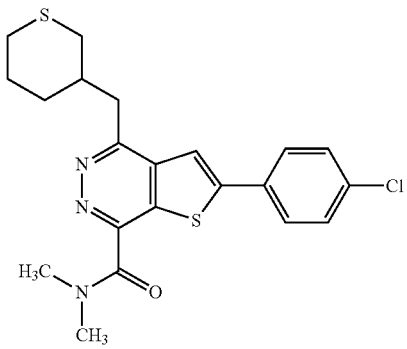

2-(4-chlorophenyl)-4-(3-tetrahydropyranmethyl)-thieno[2,3-d]pyridazinyl-7-N-methyl formamide;

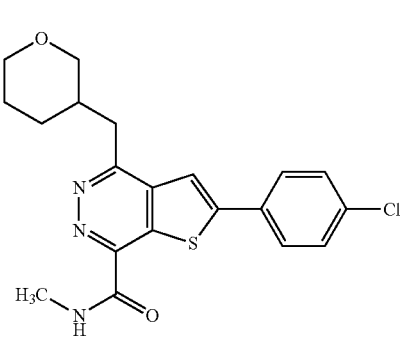

2-(4-chlorophenyl)-4-(3-tetrahydropyranmethyl)-thieno[2,3-d]pyridazinyl-7-N,N-dimethyl formamide;

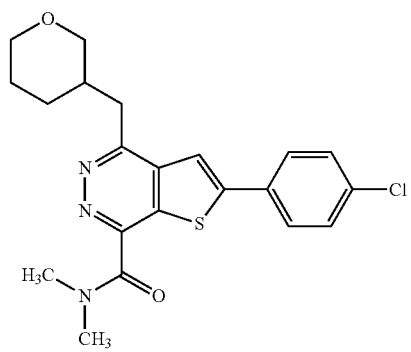

2-(4-fluorophenyl)-4-(3-pyrrolidinemethyl)-thieno[2,3-d]pyridazinyl-7-formamide;

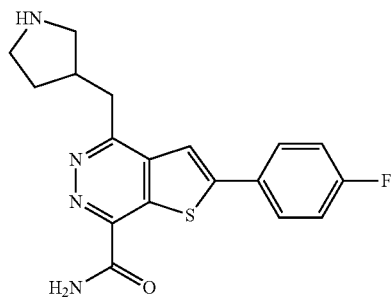
XX 2-(4-chlorophenyl)-4-(3-pyrrolidinemethyl)-thieno[2,3-d]pyridazinyl-7-formamide;

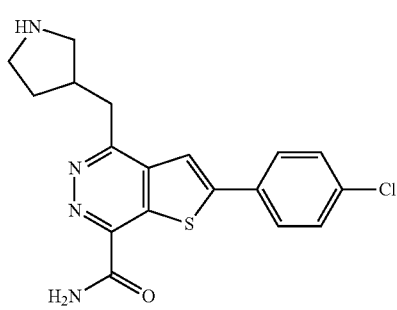
XXI 2-(4-bromophenyl)-4-(3-pyrrolidinemethyl)-thieno[2,3-d]pyridazinyl-7-formamide;

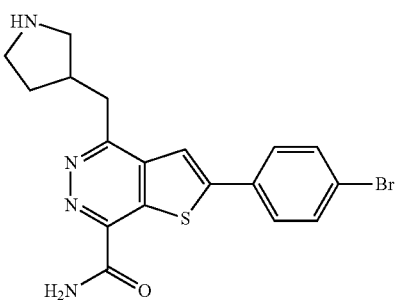
XXII 2-(4-fluorophenyl)-4-(3-tetrahydrofuranmethyl)-thieno[2,3-d]pyridazinyl-7-formamide;

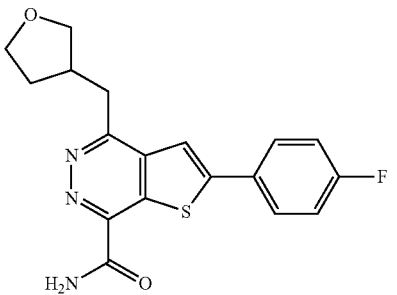
XXIII 2-(4-chlorophenyl)-4-(3-tetrahydrofuranmethyl)-thieno[2,3-d]pyridazinyl-7-formamide;

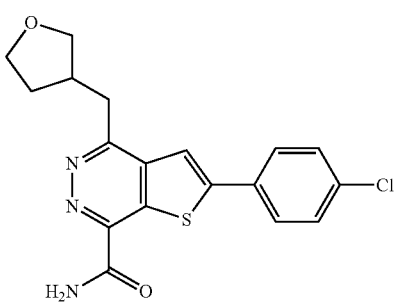
XXIV 2-(4-bromophenyl)-4-(3-tetrahydrofuranmethyl)-thieno[2,3-d]pyridazinyl-7-formamide;

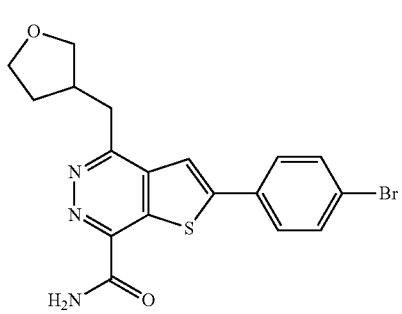
XXV 2-(4-fluorophenyl)-4-(3-tetrahydrothiophenemethyl)-thieno[2,3-d]pyridazinyl-7-formamide;

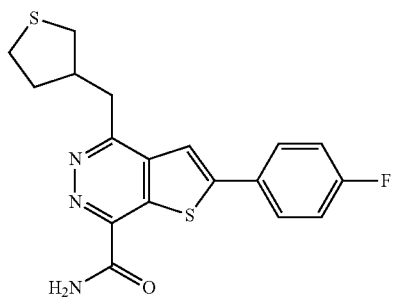
XXVI 2-(4-chlorophenyl)-4-(3-tetrahydrothiophenemethyl)-thieno[2,3-d]pyridazinyl-7-formamide;

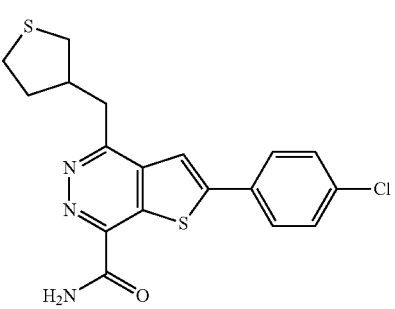
XXVII 2-(4-bromophenyl)-4-(3-tetrahydrothiophenemethyl)-thieno[2,3-d]pyridazinyl-7-formamide;

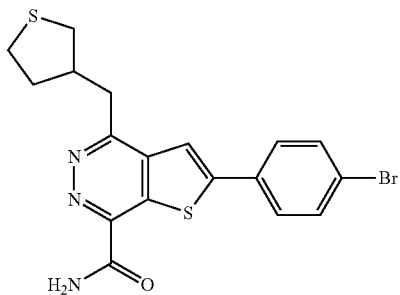

XXVIII 2-(4-chlorophenyl)-4-(3-pyrrolidinemethyl)-thieno[2,3-d]pyridazinyl-7-formamide;

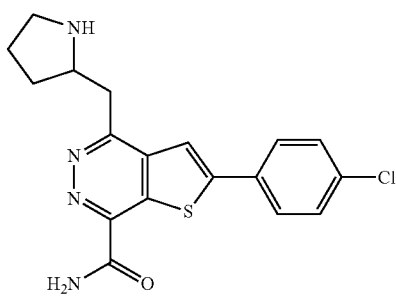

XXIX 2-(4-chlorophenyl)-4-(S-3-pyrrolidinemethyl)-thieno[2,3-d]pyridazinyl-7-formamide;

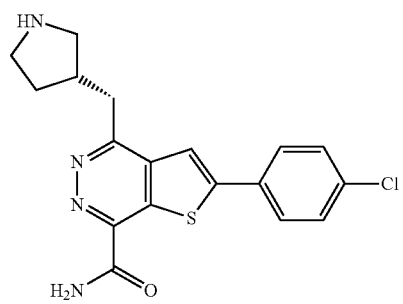

XXX 2-(4-chlorophenyl)-4-(R-3-pyrrolidinemethyl)-thieno[2,3-d]pyridazinyl-7-formamide;

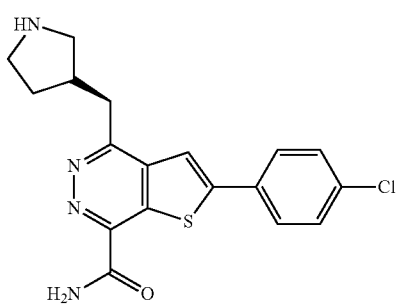

XXXI 2-(4-chlorophenyl)-4-(3-pyrrolidinemethyl)-thieno[2,3-d]pyridazinyl-7-N-methyl formamide;

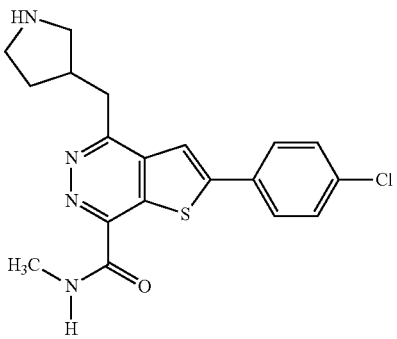

XXXII 2-(4-chlorophenyl)-4-(3-pyrrolidinemethyl)-thieno[2,3-d]pyridazinyl-7-N,N-dimethyl formamide;

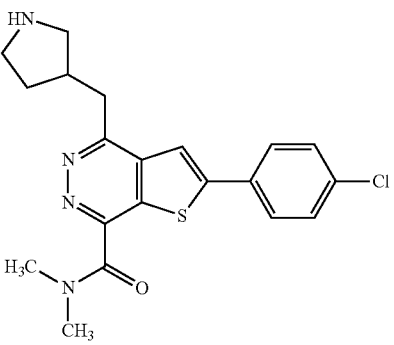

XXXIII 2-(4-chlorophenyl)-4-(3-tetrahydrothiophenemethyl)-thieno[2,3-d]pyridazinyl-7-N-methyl formamide;

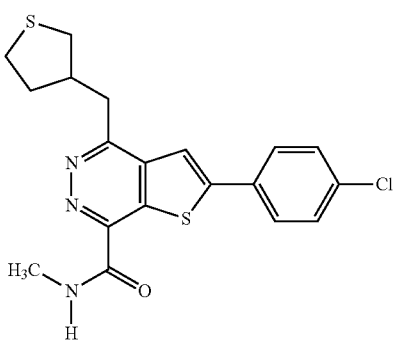

XXXIV 2-(4-chlorophenyl)-4-(3-tetrahydrothiophenemethyl)-thieno[2,3-d]pyridazinyl-7-N,N-dimethyl formamide;

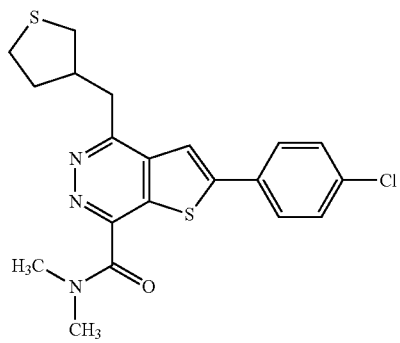

XXXV 2-(4-chlorophenyl)-4-(3-tetrahydrofuranmethyl)-thieno[2,3-d]pyridazinyl-7-N-methyl formamide;

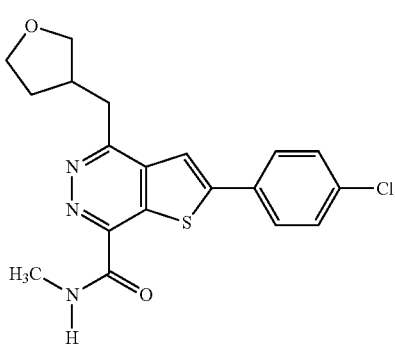

XXXVI 2-(4-chlorophenyl)-4-(3-tetrahydrofuranmethyl)-thieno[2,3-d]pyridazinyl-7-N,N-dimethyl formamide;

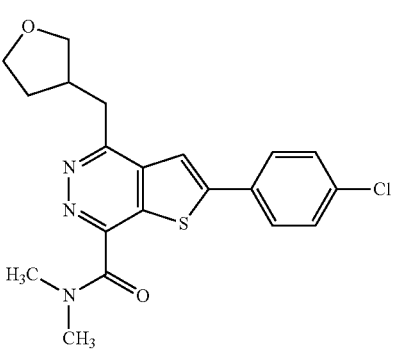

XXXVII

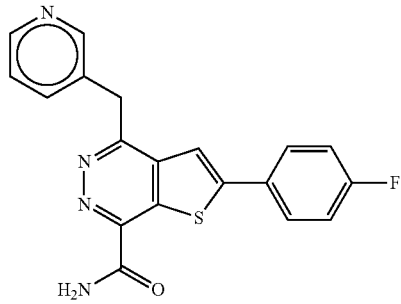

XXXVIII 2-(4-chlorophenyl)-4-(3-pyridinemethyl)-thieno[2,3-d]pyridazinyl-7-formamide;

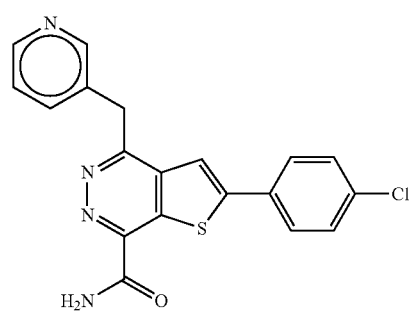

XXXIX 2-(4-bromophenyl)-4-(3-pyridinemethyl)-thieno[2,3-d]pyridazinyl-7-formamide;

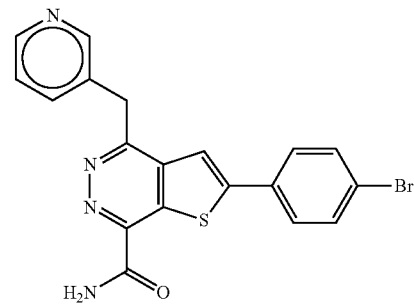

XXXX 2-(4-fluorophenyl)-4-(3-α-pyranmethyl)-thieno[2,3-d]pyridazinyl-7-formamide;

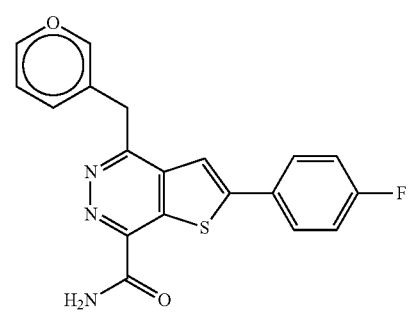

XXXXI

Preferably, R3 is pyridinyl, α-pyranyl, γ-pyranyl, α-thiopyranyl, γ-thiopyranyl, pyrrolidinyl, furanyl, or thienyl, and its optical isomers.

More preferably, the compounds of formula (I) are selected from as follows:

2-(4-fluorophenyl)-4-(3-pyridinemethyl)-thieno[2,3-d]pyridazinyl-7-formamide;

2-(4-chlorophenyl)-4-(3-α-pyranmethyl)-thieno[2,3-d]pyridazinyl-7-formamide;

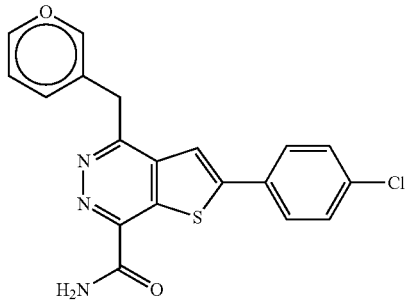

XXXXII 2-(4-bromophenyl)-4-(3-α-pyranmethyl)-thieno[2,3-d]pyridazinyl-7-formamide;

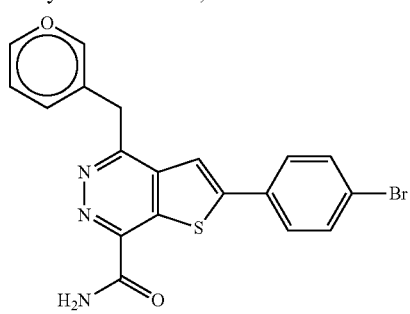

XXXXIII 2-(4-fluorophenyl)-4-(3-α-thiopyranmethyl)-thieno[2,3-d]pyridazinyl-7-formamide;

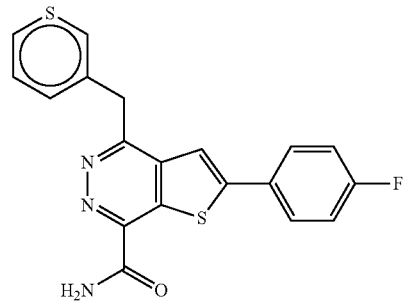

XXXXIV 2-(4-chlorophenyl)-4-(3-α-thiopyranmethyl)-thieno[2,3-d]pyridazinyl-7-formamide;

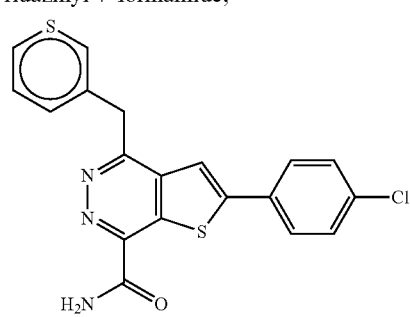

XXXXV 2-(4-bromophenyl)-4-(3-α-thiopyranmethyl)-thieno[2,3-d]pyridazinyl-7-formamide;

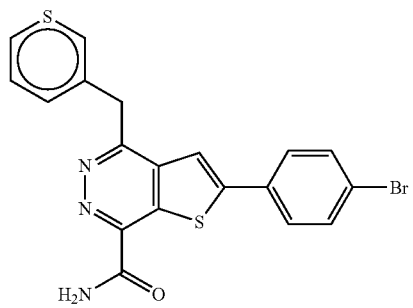

XXXXVI 2-(4-chlorophenyl)-4-(2-pyridinemethyl)-thieno[2,3-d]pyridazinyl-7-formamide;

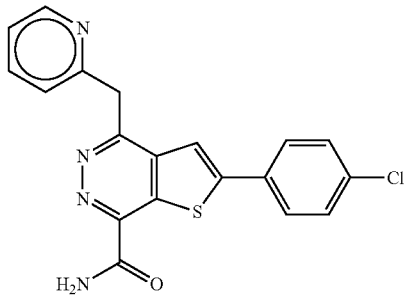

XXXXVII 2-(4-chlorophenyl)-4-(4-pyridinemethyl)-thieno[2,3-d]pyridazinyl-7-formamide;

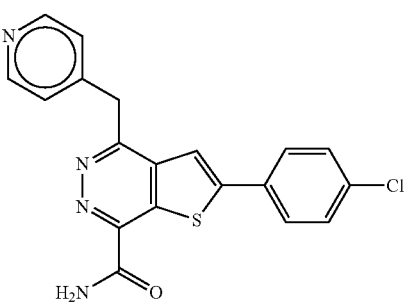

XXXXVIII 2-(4-chlorophenyl)-4-(3-pyridinemethyl)-thieno[2,3-d]pyridazinyl-7-N-methyl formamide;

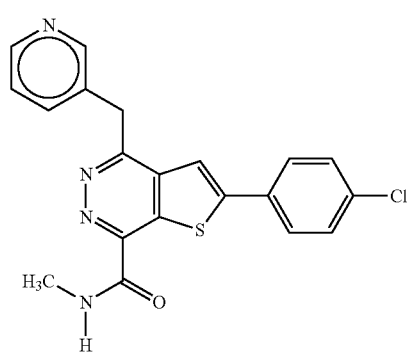

XXXXIX 2-(4-chlorophenyl)-4-(3-pyridinemethyl)-thieno[2,3-d]pyridazinyl-7-N,N-dimethyl formamide;

2-(4-chlorophenyl)-4-(3-pyranmethyl)-thieno[2,3-d]pyridazinyl-7-N-methyl formamide;

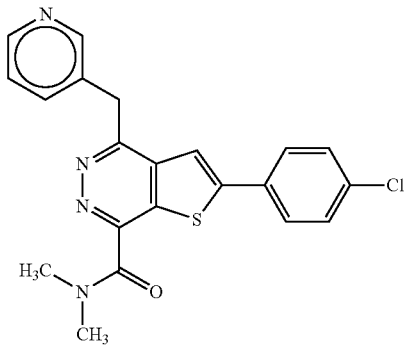

XXXXX

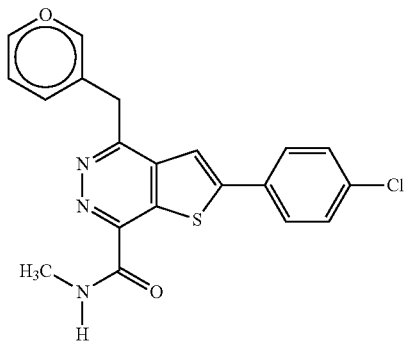

XXXXXIII 2-(4-chlorophenyl)-4-(3-thiopyranmethyl)-thieno[2,3-d]pyridazinyl-7-N-methyl formamide;

2-(4-chlorophenyl)-4-(3-pyranmethyl)-thieno[2,3-d]pyridazinyl-7-N,N-dimethyl formamide;

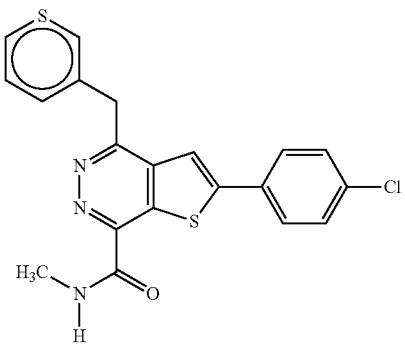

XXXXXI

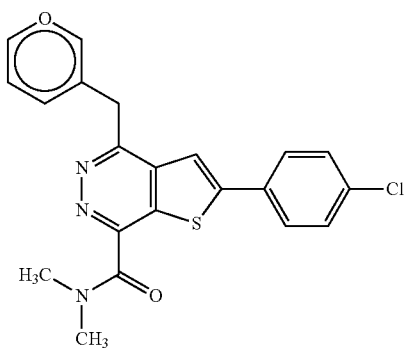

XXXXXIV 2-(4-chlorophenyl)-4-(3-thiopyranmethyl)-thieno[2,3-d]pyridazinyl-7-N,N-dimethyl formamide;

2-(4-fluorophenyl)-4-(3-pyrrolemethyl)-thieno[2,3-d]pyridazinyl-7-formamide;

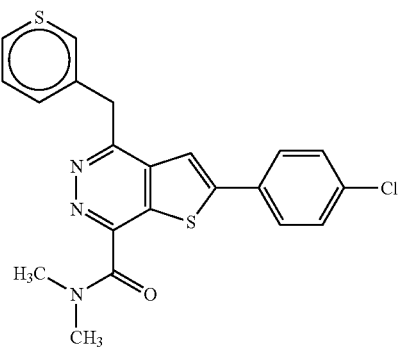

XXXXXII

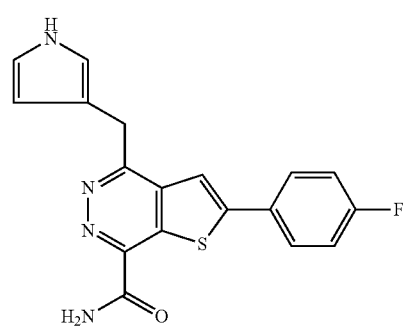

XXXXXV 2-(4-chlorophenyl)-4-(3-pyrrolemethyl)-thieno[2,3-d]pyridazinyl-7-formamide;

2-(4-chlorophenyl)-4-(3-furanmethyl)-thieno[2,3-d]pyridazinyl-7-formamide;

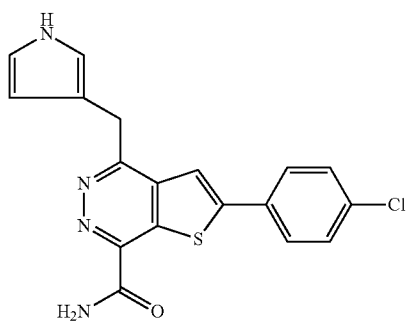
XXXXXVI

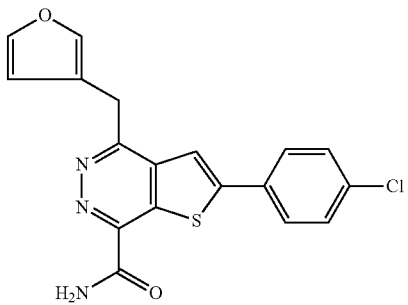
XXXXXIX 2-(4-bromophenyl)-4-(3-pyrrolemethyl)-thieno[2,3-d]pyridazinyl-7-formamide;

2-(4-bromophenyl)-4-(3-furanmethyl)-thieno[2,3-d]pyridazinyl-7-formamide;

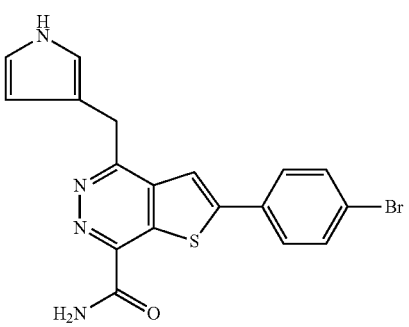
XXXXXVII

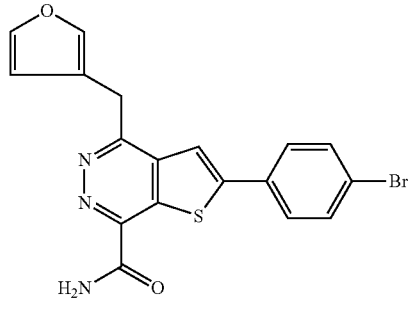
XXXXXX 2-(4-fluorophenyl)-4-(3-furanmethyl)-thieno[2,3-d]pyridazinyl-7-formamide;

2-(4-fluorophenyl)-4-(3-thiaphenemethyl)-thieno[2,3-d]pyridazinyl-7-formamide;

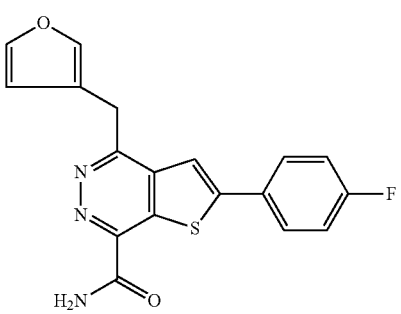
XXXXXVIII

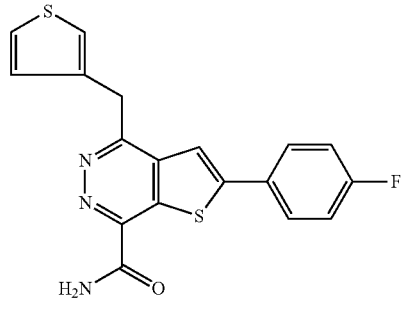
XXXXXXI 2-(4-chlorophenyl)-4-(3-thiaphenemethyl)-thieno[2,3-d]pyridazinyl-7-formamide;

2-(4-chlorophenyl)-4-(3-pyrrolemethyl)-thieno[2,3-d]pyridazinyl-7-N-methyl formamide;

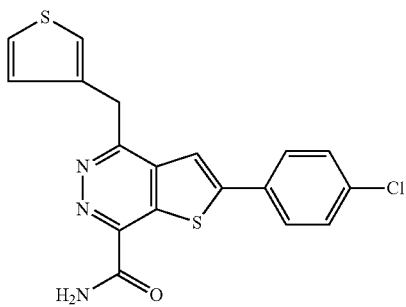

XXXXXXII

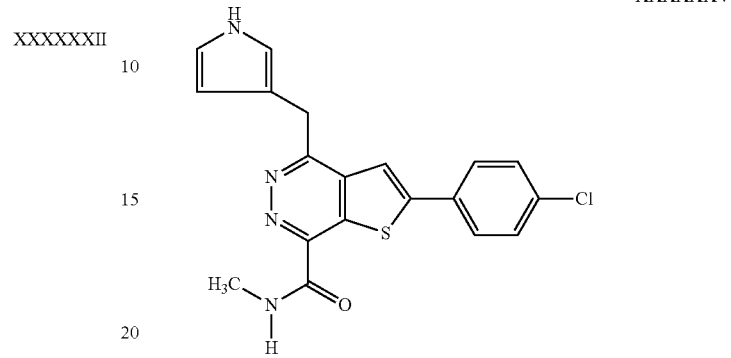

XXXXXXV 2-(4-bromophenyl)-4-(3-thiaphenemethyl)-thieno[2,3-d]pyridazinyl-7-formamide;

2-(4-chlorophenyl)-4-(3-pyrrolemethyl)-thieno[2,3-d]pyridazinyl-7-N,N-dimethyl formamide;

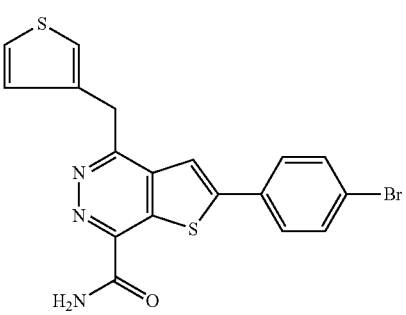

XXXXXXIII

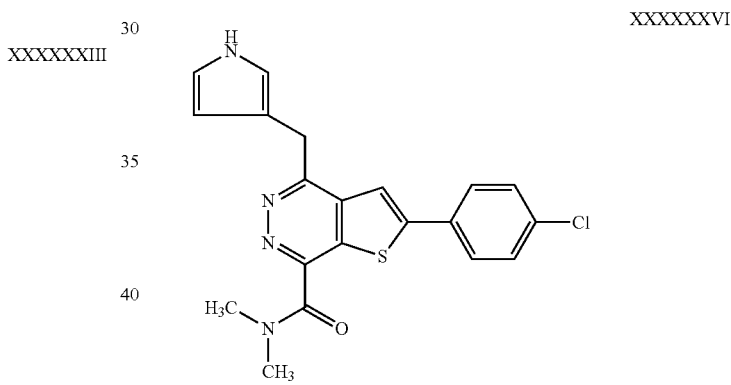

XXXXXXVI 2-(4-chlorophenyl)-4-(2-pyrrolemethyl)-thieno[2,3-d]pyridazinyl-7-formamide;

2-(4-chlorophenyl)-4-(3-thiaphenemethyl)-thieno[2,3-d]pyridazinyl-7-N-methyl formamide;

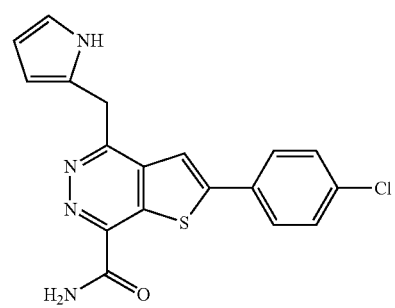

XXXXXXIV

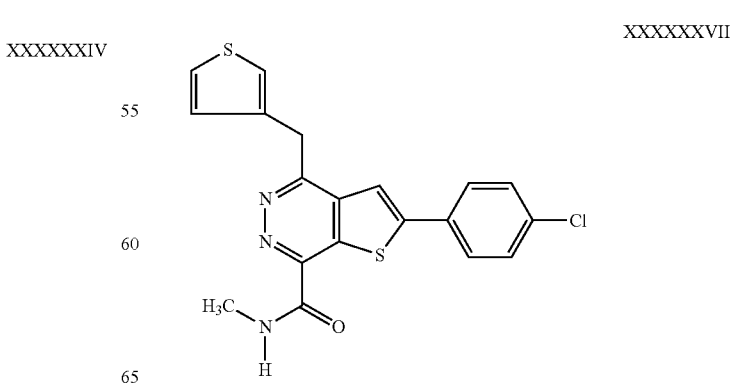

XXXXXXVII 2-(4-chlorophenyl)-4-(3-thiaphenemethyl)-thieno[2,3-d]pyridazinyl-7-N,N-dimethyl formamide;

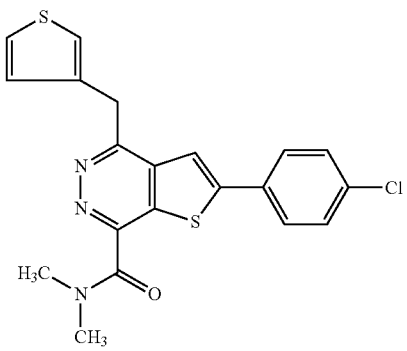

XXXXXXVIII 2-(4-chlorophenyl)-4-(3-furanmethyl)-thieno[2,3-d]pyridazinyl-7-N-methyl formamide;

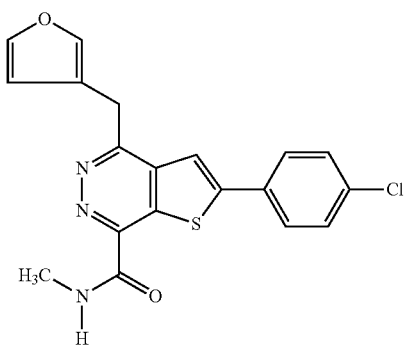

XXXXXXIX 2-(4-chlorophenyl)-4-(3-furanmethyl)-thieno[2,3-d]pyridazinyl-7-N,N-dimethyl formamide;

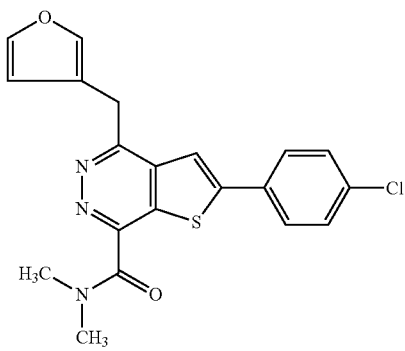

XXXXXXX 2-(3,5-dichlorophenyl)-4-(3-piperidinemethyl)-thieno[2,3-d]pyridazinyl-7-formamide;

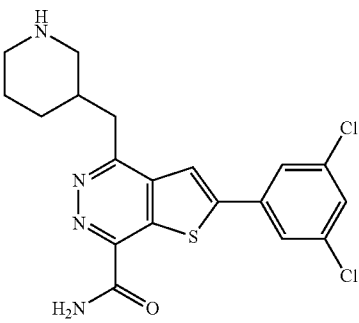

XXXXXXXI

In accordance with another aspect of the present invention, a pharmaceutical composition is provided, including compounds of formula (I) having a therapeutically effective amount and its pharmaceutically acceptable salts or hydrates, and pharmaceutically acceptable carriers.

The pharmaceutical compositions of the present invention can be locally administered such as at lung, head, colon and so on in the form of solution, suspension, aerosol or dry power and so on; or systematically administered such as oral administration in the form of tablets, power, or parenterally administered in the form of solution or suspension, or subcutaneous administration, or rectal administration in the form of suppository, or percutaneous administration.

In accordance with another aspect of the present invention, uses of the compounds of formula (I) or pharmaceutically acceptable salts or hydrates thereof in the preparation for medicaments of treatment or prophylaxis of tumor diseases are provided. Wherein said tumor diseases include cervical tumor, tumor of head and neck, carcinoma of breast, ovary, lung (non small cell), pancreas, colon, prostate or other tissues, as well as leukemias and lymphomas, tumors of central and peripheral nervous system and other tumors such as melanoma, fibrosarcoma and osteosarcoma.

In accordance with further aspect of the present invention, uses of the compounds of formula (I) or pharmaceutically acceptable salts or hydrates thereof in preparation for medicaments of treatment or prophylaxis of proliferative diseases are provided. Wherein said proliferative diseases include autoimmune, inflammatory, neurological and cardiovascular diseases.

In accordance with one aspect of the present invention, uses of the compounds of formula (I) or pharmaceutically acceptable salts or hydrates thereof in the preparation for medicaments of limiting cell proliferation of human or animals are provided.

In accordance with still another aspect of the present invention, uses of the compounds of formula (I) or pharmaceutically acceptable salts or hydrates thereof in the preparation for medicaments of inhibiting the tumors or kinases associated with growth factors are provided.

For the above mentioned uses, the dosage depends on compounds used, administration approaches, required treatment diseases.

In accordance with last aspect of the present invention, methods of the compounds of formula (I) or pharmaceutically acceptable salts or hydrates thereof are provided, and the method includes the following steps:

In the presence of alkali, the compound of formula A is treated with dialkyl oxalates:

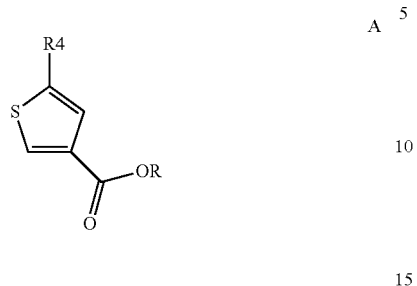

then is treated with hydrazine, to produce the compound of formula B:

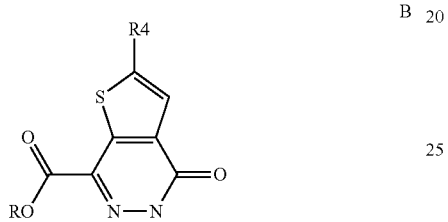

the compound of formula B is treated with phosphorus oxychloride, to produce the compound of formula C:

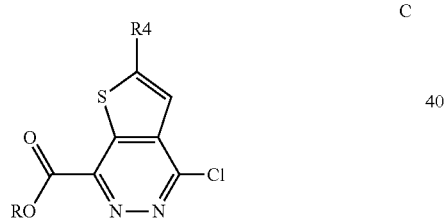

and the compound of formula C is reacted with the compound $R_3CH_2$, to produce the compound of formula D,

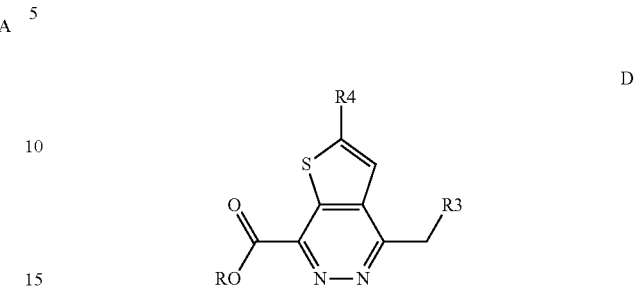

and then the compound of formula D is reacted with NHR1R2, the protecting group on R3 is then removed and treated with an alkaline, to produce the compounds of formula (I) or pharmaceutically acceptable salts or hydrates thereof,

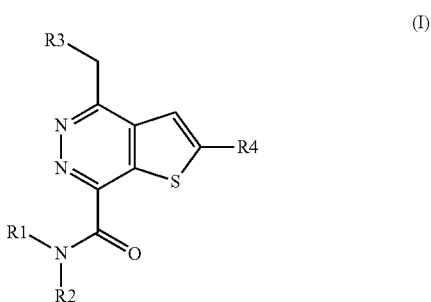

wherein R is a $C_{1-4}$ alkyl, and R1 and R2 are independently H or $C_{1-4}$ alkyl respectively; R3 is a saturated or unsaturated 6- or 5-membered ring containing N, S or O, and its optical isomers; R4 is a halophenyl monosubstituted or disubstituted at any position.

The synthesis process of the present invention is described below:

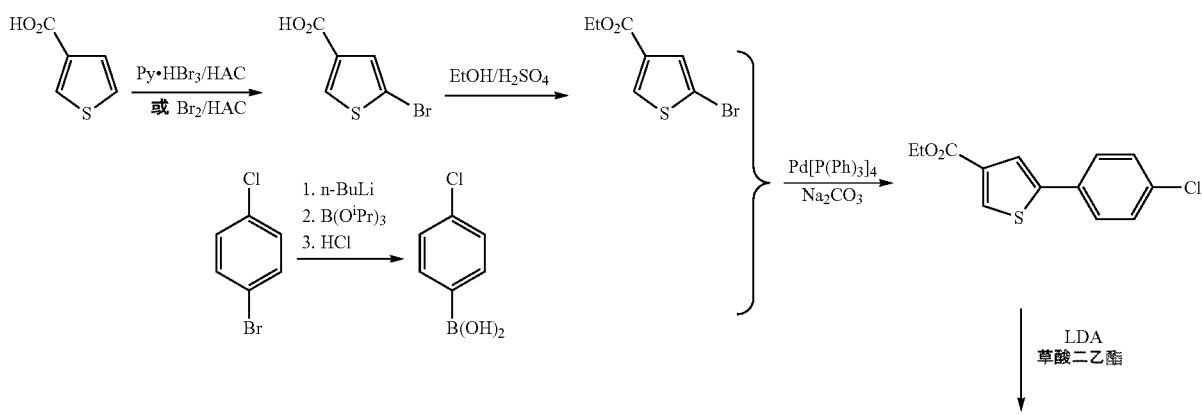

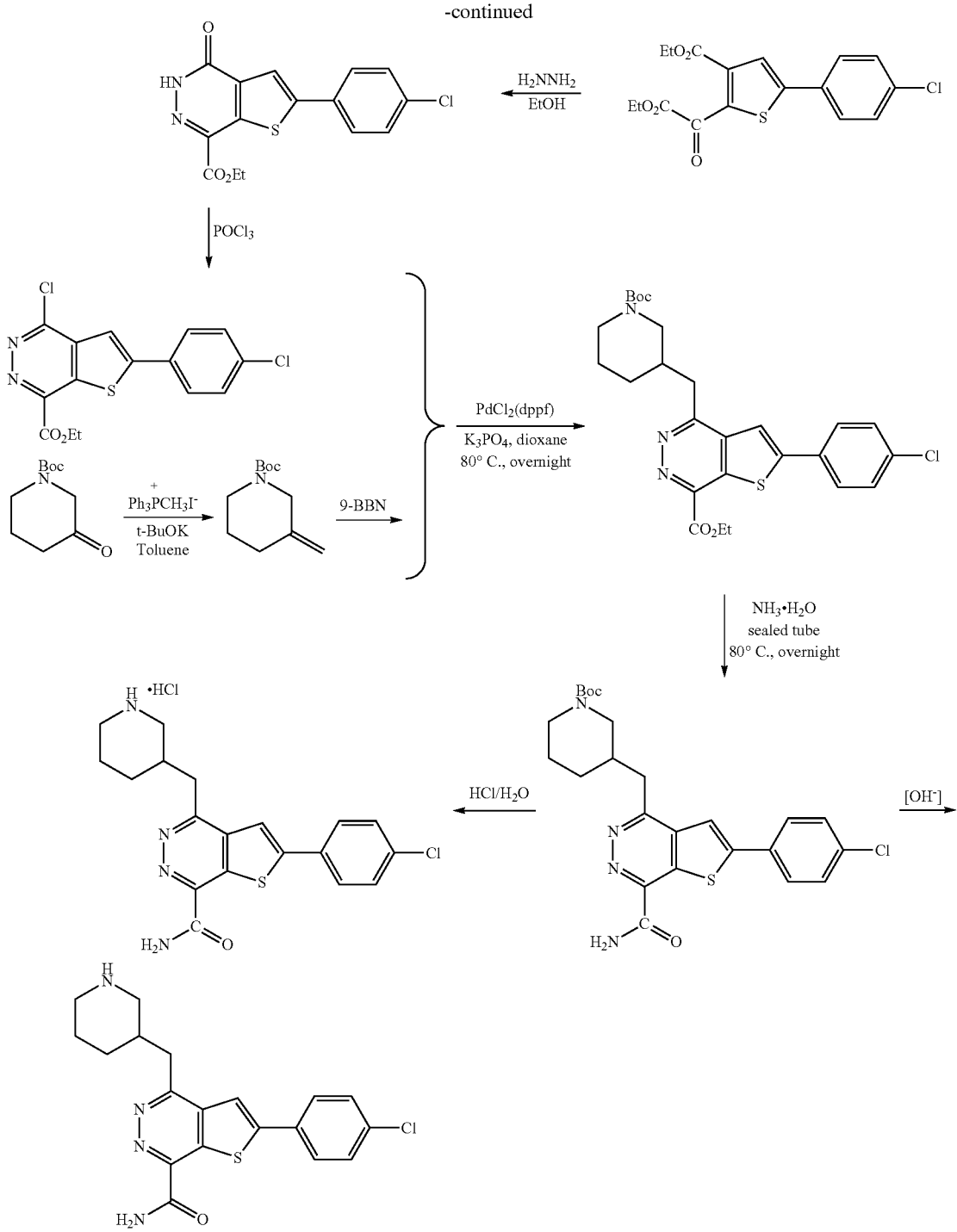

The synthesis process of 2-(4-chlorophenyl)-4-(3-piperidinemethyl)-thieno[2,3-d]pyridazinyl-7-formamide.

Wherein, the compound of formula A may be prepared by conventional chemical methods in the field or purchased commercially. After being obtained, the compound of formula A is condensed with dialkyl oxalates, e.g. diethyl oxalate, in the presence of alkali such as common alkali LDA (lithium diisopropylamide) and common organic solvents such as tetrahydrofuran, to produce the compound Y. The condensation reaction should be proceeded at a low temperature due to the presence of LDA. It is easy for persons skilled in the art to obtain LDA which is generally fresh prepared at a low temperature.

Then, compound Y is reacted with hydrazine such as $H_2NNH_2$ in alcoholic solvent to produce the compound of formula B.

The compound of formula B is treated with phosphorus oxychloride for an acylation reaction to produce the compound of formula C.

The above three steps refer to a synthesis method of intermediate of thienopyridazine compound produced by F. Hoffman-La Roche AG. in WO2005105808.

The compounds of R3CH₂ with a Boc protecting group are prepared by conventional methods in the field, and heated at the reaction temperature of 80~90° C. in the presence of catalysts such as PdCl₂ (dppf) and solvents such as phosphates/1,4-dioxane, the compound of formula C is reacted with R3CH₂ containing a Boc protecting group for overnight to produce the compound of formula D. In the above reactions, the compounds of R3CH₂ should be pretreated with 9-BBN, please refer to the coupling reaction of "Suzuki-Miyaura", p 6125-6128, Tetrahedron Letters 45(2004).

The compoundS of formula D and HNR1R2 are ammonolyzed in a sealed container using conventional methods with the reaction solvents of 1,4-dioxane, under heating at temperature of 80° C. for overnight, then the Boc protecting group on R3 is removed under acidic conditions to obtain the acid salts of formula (I), and adjust pH with alkali to produce the compounds of formula (I).

The raw materials of the above mentioned preparations are either obtained by commercial suppliers or are prepared by conventional methods in the field.

DETAILED DESCRIPTION OF THE INVENTION

Hereafter, the present invention will be described specifically with reference to examples. The examples are given only for illustration of the technical solution of the present invention and should not be construed to limit the present invention.

Where, the structure of the compounds of formula (I) is determined by nuclear magnetic resonance (NMR) and mass-spectrometric techniques; the proton NMR chemical shifts are measured using δ scale, and the peak multiplicity is represented as follows: s, single peak; m, multiple peak. The intermediate is generally represented by mass spectrometry and NMR.

EXAMPLE 1

2-(4-chlorophenyl)-4-(3-piperidinemethyl)-thieno[2,3-d]pyridazinyl-7-formamide

Step 1: Synthesis of 5-bromo-thiophene-3-formic acid

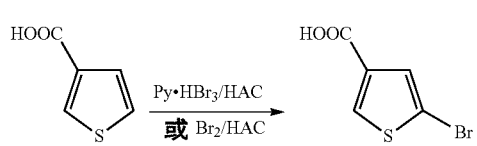 [SMILES: O=C(O)c1ccsc1 ; O=C(O)c1csc(Br)c1]

Thiophene-3-formic acid (12.6 g) and AcOH (96 ml) are added to a reaction flask (250 ml), to dissolved after stirred at room temperature, HBr solution (8 ml) is then added to the reaction flask, and the reaction is rapidly changed to a light yellow. Pyridinium bromide perbromide (27 g) is then added to the flask in batches at room temperature. After addition, the reaction is stirred at room temperature, and the reaction is tracked by HPLC. The above mixture is poured into ice-water after reaction, stirred for about 30 minutes, filtered to form a white powder solid, the white powder solid is crystallized with hot water, filtered and dried to obtain a crystal of 5-bromo-thiophene-3-formic acid (10.8 g), content of 92% measured by HPLC.

Thiophene-3-formic acid (12.5 g), AcOH (83 ml) are added to a reaction flask (500 ml), stirred at room temperature and dissolved to obtain a colorless transparent liquid. A solution of Br₂ (5.4 ml) in AcOH (100 ml) is placed in a constant pressure funnel and dropped to the reaction flask at room temperature and kept at a temperature below 25° C. After addition, the reaction is carried out at room temperature overnight. The reaction mixture is poured into ice-water next day, stirred for about 30 minutes, filtered to form a white powder solid. The white powder solid is crystallized with hot water, filtered and dried to obtain a white crystal of 5-bromo-thiophene-3-formic acid (10 g), content of 92% measured by HPLC.

Step 2: Synthesis of 5-bromo-thiophene-3-ethyl formate

5-bromo-thiophene-3-formic acid (18.5 g) obtained by the above step, absolute ethanol (150 ml) and concentrated sulfuric acid (5 ml) are added into a three mouth flask (500 ml) and heated under reflux, and vaporized under reduced pressure to remove solvent after reaction. Then ethyl acetate (100 ml) and saturated brine (200 ml) are added, and stirred, placed for layer separation. The aqueous layer is reextracted with ethyl acetate (25 ml×2) twice. The organic phase is combined together and transferred to a separatory funnel. Sodium carbonate solution (10%) is added to the separatory funnel to adjust pH≈8 and then separated, and a organic phase is washed with a saturated brine to pH=7, and dried with anhydrous magnesium sulfate over night, and filtered next day, and vaporized under reduced pressure to remove solvent to obtain a light yellow oil-liquid of 5-bromo-thiophene-3-ethyl formate (15 g).

Step 3: Synthesis of 4-chlorophenylboric acid

4-Bromochlorobenzene (70.6 g) is added into a four mouth flask connecting with a mechanical stirring apparatus, two constant pressure funnels and a temperature probe. Toluene (588.3 ml) and tetrahydrofuran (THF) (147 ml) are added under stirring at room temperature under argon, and dissolved to obtain a colorless transparent liquid. Then triisopropyl borate (109.2 ml) and n-butyllithium (176.4 ml, 2.5M in hexane) are respectively added into two constant pressure funnels, and cooled the inner temperature to below −78° C., then n-butyllithium solution is dropped to the flask under controlling a dropping speed to keep the inner temperature below −78° C. After addition, the mixture is kept at the temperature for 1 hour, then triisopropyl borate is dropped into the mixture under the temperature below −78° C., and kept at the temperature for 1 hour after addition, and then the cooling system is removed to naturally warm up to −20° C. HCl solution (360.4 ml, 2.2M) is added to the mixture to warm up to about 10° C., and then placed for layer separation. The aqueous phase is reextracted with toluene (58.8 ml, 2 times). The organic phase is combined together and washed with saturated brine to pH=7 to obtain a colorless transparent liquid, dried with anhydrous sodium sulfate, filtered, and evaporated under reduced pressure to remove most of solvents and the white solid is finally precipitated, filtered to obtain a crystal of 4-chlorophenylboric acid (48 g).

Step 4: Synthesis of
5-(4-chlorophenyl)-thiophene-3-ethyl formate

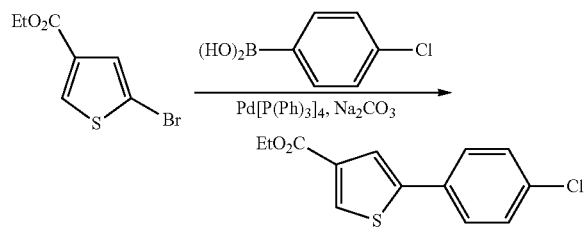

5-(4-chlorophenyl)-thiophene 3-ethyl formate (10.5 g), 4-chlorophenylboronic acid (6 g), Pd[P(Ph)$_3$]$_4$ (1.5 g), sodium carbonate (7.5 g) and a solvent mixture of toluene:water:EtOH (4:2:1, v/v) are in turn added to a three mouth flask (500 ml) and heated at reflux for 3 hours, the reaction is tracked by TLC. The reaction mixture is cooled to a room temperature after reaction, and placed for layer separation. The aqueous phase is reextracted with toluene (35 ml, 2 times). The organic phase is combined together and washed with saturated brine to pH=7, dried with anhydrous sodium sulfate over night and filtered next day, and then evaporated under reduced pressure to remove solvents to obtain a light yellow viscous fluid, and placed to obtain a clotted solid, and recrystallized with absolute EtOH to obtain a crystal of 5-(4-chlorophenyl)-thiophene-3-ethyl formate (8.6 g).

$^1$HNMR (500 MHz, DMSO), δ 8.30 (sc, 1H), 7.81 (s, 1H), 7.72 (m, 2H), 7.46 (m, 2H), 4.27 (m, 2H), 1.30 (m, 3H).

Step 5: Synthesis of 5-(4-chlorophenyl)-2-ethoxyoxalyl-thiophene-3-ethyl formate

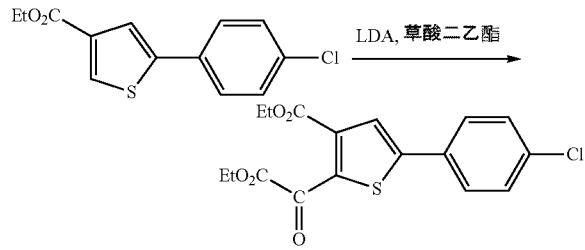

Preparation of LDA: THF (252.6 ml) and N,N-diisopropylamine (79 ml) are added into a three mouth flask (1000 ml) under argon, and n-butyllithium (302.8 ml, 1.6M in hexane) is placed to a constant pressure funnel (500 ml) and dropped into the flask when the inner temperature is below −20° C. with an intensely exothermic reaction, and kept −20° C.~−30° C. of the inner temperature under controlling an adding speed; after addition, the above mixture naturally is warmed up to a room temperature directly used for the following condensation reaction.

Condensation reaction: 5-(4-chlorophenyl)-3-thiophene-ethyl formate (28.7 g), THF (1084 ml) and diethyl oxalate (29.7 ml) are added into a four mouth flask (2000 ml) connecting with the mechanical stirring apparatus, two constant pressure funnels and a temperature probe. The mixture is stirred at room temperature and dissolved to obtain a light yellow transparent liquid. LDA solution prepared by the above step is transferred into a constant pressure funnel and cooled to a temperature below −78° C., and LDA is dropped to the flash under argon at the temperature below −78° C. under controlling a dropping speed, after addition, the reaction is tracked by TLC. HCl solution (2.2M) is added to the flash after reaction and adjusted to pH≈3, and a color of the reaction liquid is changed from reddish brown into orange. The temperature is warmed up to about 0° C., a solid NaCl is then added, and stirred to desolve, and placed for layer separation. The aqueous phase is reextracted with THF (143.5 ml, 2 times). The organic phase is combined together and washed with saturated brine for two times, and then adjusted to pH≈8 with diluted sodium carbonate solution; finally, washed with saturated brine to pH=7, dried with anhydrous sodium sulfate, filtered and evaporated under reduced pressure to remove solvent to obtain a light yellow viscous fluid, and placed at room temperature to gradually become a solid, and recrystallized with EtOH to obtain a pure product of 5-(4-chlorophenyl)-2-ethoxyoxalyl-thiophene-3-ethyl formate (orange crystal, 25.5 g).

$^1$HNMR (500 MHz, CD$_3$Cl), δ 7.61 (s, 1H), 7.59 (m, 2H), 7.42 (m, 2H), 4.37 (m, 4H), 1.39 (m, 6H).

Step 6: Synthesis of 2-(4-chlorophenyl)-4-oxo-4,5-dihydro-thiero[2,3-d]pyridazinyl-7-ethyl formate

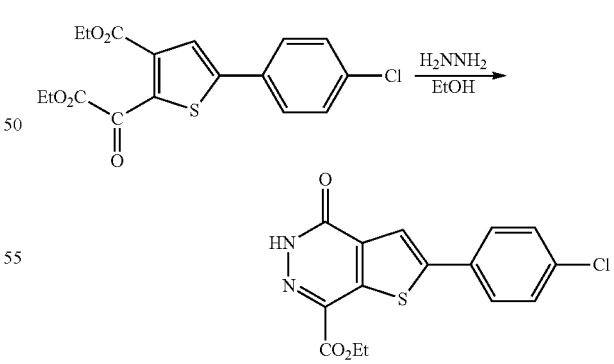

A crystal of 5-(4-chlorophenyl)-2-ethoxyoxalyl-thiophene-3-ethyl formate (3.0 g), absolute ethanol (45 ml) are added into a reaction flask (100 ml), stirred at room temperature to obtain a yellow suspension. Hydrazine hydrate (0.75 ml) is added into a constant pressure funnel, stirred for 10 minutes and then dropped to the reaction flask. The yellow suspension is dissolved to a transparent liquid, and the above mixture is heated at 70° C. and a yellow solid in the flask is gradually precipitated with rise of the temperature, and the reaction liquid became increasingly viscous. The reaction mixture is kept for 1 h and then cooled to a room temperature, and filtered to obtain a pistachio solid, and the pistachio solid is respectively washed with a mixture of hexane/dichloromethane (1:1)(15 ml, 2 times) and methanol/dichloromethane (1:1)(15 ml, 2 times) and dried under reduced pressures to obtain 2-(4-chlorophenyl)-4-oxo-4,5-dihydro-thiero[2,3-d]pyridazinyl-7-ethyl formate (2.75 g).

Step 7: Synthesis of 4-chloro-2-(4-chlorophenyl)-thieno[2,3-d]pyridazinyl-7-ethyl formate

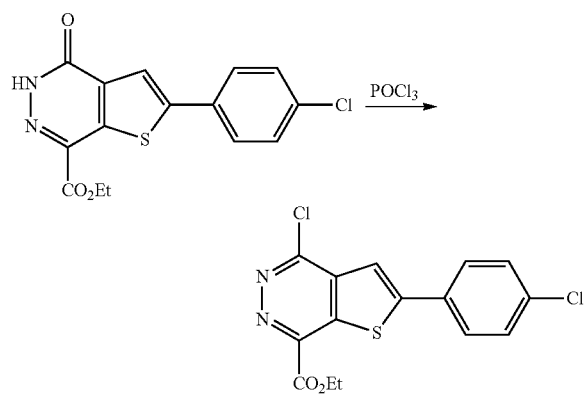

2-(4-chlorophenyl)-4-oxo-4,5-dihydro-thiero[2,3-d]pyridazinyl-7-ethyl formate (1.5 g), phosphorous oxychloride (22.5 ml) are added to a three mouth flask (100 ml), heated at 95° C. for 3 h, and dissolved to obtain a dark red brown solution. After reaction, the solution is cooled to a room temperature and evaporated under reduced pressures to remove solvent to obtain a chocolate brown viscous fluid. Tetrahydrofuran and a saturated brine are added to the fluid and stirred, and many yellow solids are precipitated, then filtered, placed for layer separation and reextracted; adjusted to pH≈9 with a diluted sodium carbonate solution after the organic phase is combined together; finally, washed with a saturated brine to pH=7, and dried with anhydrous sodium sulfate, filtered, decolourised with active carbon at reflux to obtain a light yellow green liquid; and the fluid is evaporated under reduced pressure to remove solvent to obtain 4-chloro-2-(4-chlorophenyl)-thieno[2,3-d]pyridazinyl-7-ethyl formate (light green flocculent solid, 1.0 g).

$^{1}$HNMR (500 MHz, CD$_{3}$Cl), δ 7.74 (m, 3H), 7.59 (m, 2H), 4.65 (m, 2H), 1.55 (m, 3H). HRMS (high resolution MS) MW=351.98.

Step 8: Synthesis of N-Boc-3-methylene piperidine

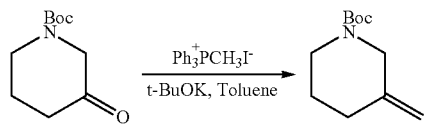

Triphenylmethyl phosphonium iodide (22.14 g) and toluene (135 ml) are added into a three mouth flask (500 ml), stirred at room temperature to obtain a milky white suspension and quickly changed to orange after potassium tert-butanolate (5.31 g) is added. Then N-Boc-3-piperidone (6.0 g) in toluene (66 ml) is added into a constant pressure funnel and dropped into the flask under argon with obvious exothermic phenomenon, and kept at the temperature of 30° C. and the reaction is tracked by TLC after addition. After reaction, the mixture is filtered and washed with a saturated brine (200 ml, 2 times) and then adjusted to pH≈3 with diluted HCl (1M), and then washed with a saturated brine to pH=7, dried with anhydrous sodium sulfate, and filtered to obtain a yellow transparent liquid. The yellow transparent liquid is purified together with silica gel by chromatography (elution liquid: petroleum ether:ethyl acetate=15:1) to obtain a yellow oil-liquid of N-Boc-3-methylene piperidine (4.2 g).

$^{1}$HNMR (400 MHz, CD$_{3}$Cl), δ 4.83 (s, 1H), 4.76 (s, 1H), 3.89 (s, 2H), 3.45 (m, 2H), 2.26 (m, 2H) 1.64 (s, 2H), 1.51 (s, 9H).

Step 9: Synthesis of 4-(1-Boc-3-piperidinemethyl)-2-(4-chlorophenyl)-thieno[2,3-d]pyridazinyl-7-ethyl formate

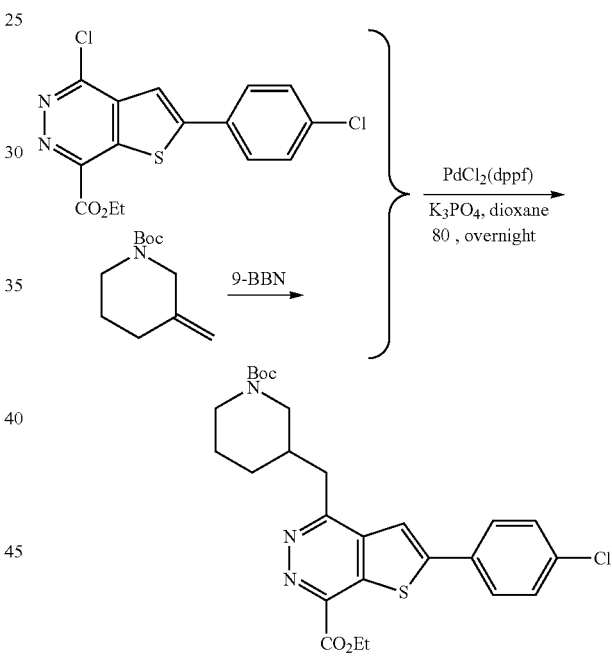

N-Boc-3-methylene pyrazdine (0.4 g) is added into a three mouth flask under argon and cooled to 0° C. 9-BBN solution (12 ml, 0.5M in THF) is injected into the reaction flask with a syringe and kept for 30 min, and then warmed up to room temperature for 2 h, and evaporated to remove solvent under a reduced pressure (25° C.). 1,4-dioxane (20 ml), PdCl$_{2}$(dppf) (0.05 g), potassium phosphate (0.32 g) and 4-chloro-2-(4-chlorophenyl)-thieno[2,3-d]pyridazinyl-7-ethyl formate are added to the reaction flask and heated at 90° C. over night. The reaction mixture is cooled to room temperature next day, then addition of ice water (50 ml) and ethyl acetate (50 ml), and then stirred for about 15 min, and placed for layer separation. The water layer is reextracted with ethyl acetate for 3 times, the organic phase is combined together and washed with a saturated brine to pH=7, dried with anhydrous magnesium sulfate and filtered. The filtered liquid is purified with silica gel by chromatography (ethyl acetate:petroleum ether=1:5) to obtain an orange viscous fluid (0.6 g), and ethanol (2 ml) is added to the fluid and crystallized in refrigerator to obtain a solid of 4-(1-Boc-3-piperidinemethyl)-2-(4-chlorophenyl)-thieno[2,3-d]pyridazinyl-7-ethyl formate (0.3 g).

$^1$HNMR (400 MHz, DMSO), δ 8.90 (s, 1H), 8.03 (m, 2H), 7.63 (m, 2H), 4.54 (m, 2H), 3.73 (s, 2H), 3.32 (m, 2H), 3.28 (m, 1H), 2.82 (m, 2H), 2.09 (s, 1H), 1.78 (s, 1H), 1.64 (s, 1H), 1.44 (m, 3H), 1.39 (s, 1H), 1.32 (s, 9H).

MS (EI): 515 (M+), 486, 458, 442, 414, 334, 332, 306, 304, 149, 57.

Step 10: Synthesis of 4-(1-Boc-3-piperidinemethyl)-2(4-chlorophenyl)-7-aminocarbonyl-thieno[2,3-d]pyrida-zine

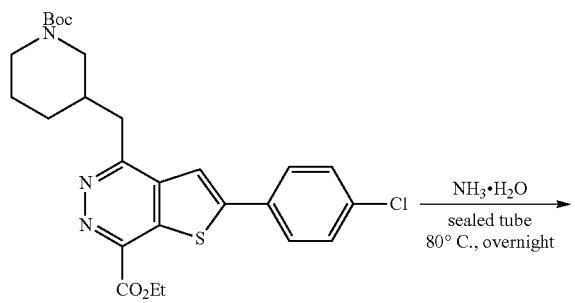

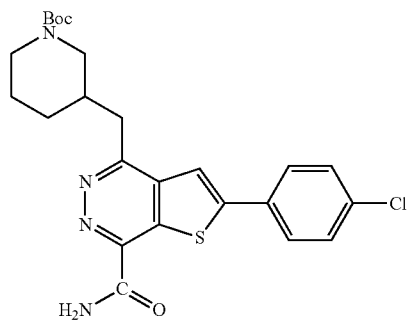

4-(1-Boc-3-piperidinemethyl)-2-(4-chlorophenyl)-thieno[2,3-d]pyridazinyl-7-ethyl formate (0.3 g), 1,4-dioxane (5 ml) and NH$_3$.H$_2$O (5 ml) are added to a sealed tube (25 ml) and heated at 80° C. over night. The reaction mixture is cooled to room temperature and transferred into a separating funnel next day, and addition of ethyl acetate, vibrated, and placed for layer separation. The water layer is reextracted with ethyl acetate for 2 times, the organic phase is combined together and adjusted to pH≈3 with 1M HCl solution, and then washed with saturated brine to pH=7, dried with anhydrous magnesium sulfate and filtered. The filtered liquid is purified with silica gel by chromatography (ethyl acetate:petroleum ether=1:5) to obtain a solid of 4-(1-Boc-3-piperidinemethyl)-2(4-chlorophenyl)-7-aminocarbonyl-thieno[2,3-d]pyridazine (0.22 g)

$^1$HNMR (500 MHz, CDCl$_3$), δ 8.10 (s, 1H), 7.77 (m, 2H), 7.66 (s, 1H), 7.48 (m, 2H), 5.90 (s, 1H), 4.05 (s, 1H), 3.88 (m, 1H), 3.31 (m, 1H), 3.21 (m, 1H), 2.81 (m, 2H), 2.28 (s, 1H), 1.81 (s, 1H), 1.67 (s, 3H), 1.39 (s, 9H).

MS (ESI): 487 (M+1).

Step 11: Synthesis of 2-(4-chlorophenyl)-4-(3-piperidinemethyl)-thieno[2,3-d]pyridazinyl-7-formamide hydrochloride

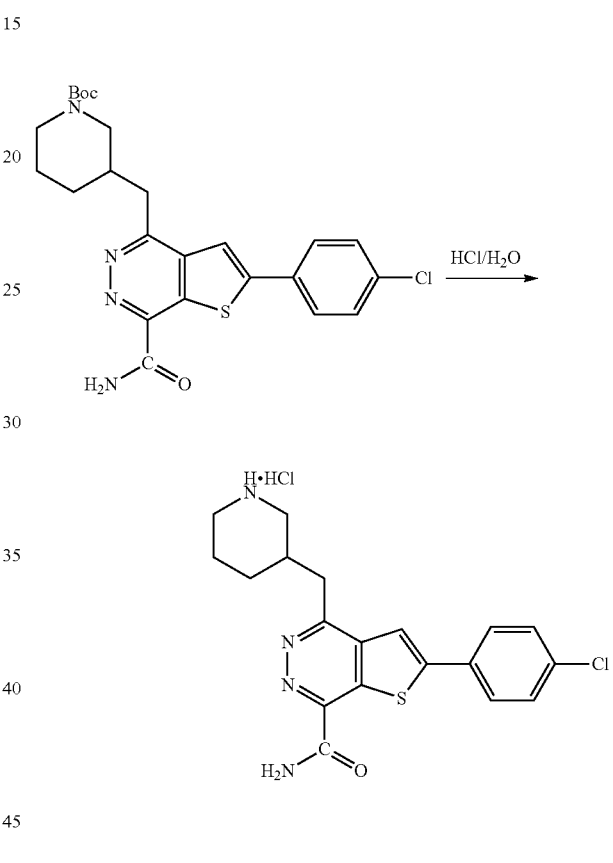

4-(1-Boc-3-piperidinemethyl)-2(4-chlorophenyl)-7-aminocarbonyl-thieno[2,3-d]pyridazine (200 g) and ethyl acetate (4 ml) are added to a single mouth flask (25 ml) and dissolved to a light yellow transparent solution, addition of HCl (4 ml, 3M) and the solution is quickly changed to a white suspension, heated at 30° C. for 1 h, and the suspension is changed to transparent and the reaction is tracked by plate; after reaction, the above mixture is evaporated under reduced pressure to remove solvent to obtain a solid of 2-(4-chlorophenyl)-4-(3-piperidinemethyl)-thieno[2,3-d]pyridazinyl-7-formamide hydrochloride (100 mg).

$^1$HNMR (500 MHz, DMSO), δ9.51 (m, 1H), 9.09 (m, 1H), 8.79 (s, 1H), 8.66 (s, 1H), 8.29 (s, 1H), 8.08 (m, 2H), 7.62 (m, 2H), 3.45 (m, 2H), 3.4 (m, 1H), 3.17 (m, 1H), 2.79 (m, 2H), 2.52 (m, 1H), 1.81 (m, 2H), 1.77 (m, 1H), 1.42 (m, 1H).

MS (ESI): 387 (M+1).

Step 12:

Synthesis of 2-(4-chlorophenyl)-4-(3-piperidinemethyl)-thieno[2,3-d]pyridazinyl-7-formamide

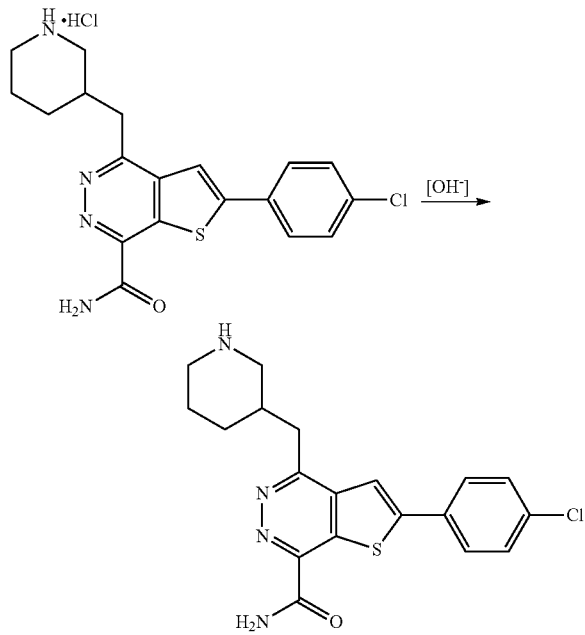

2-(4-chlorophenyl)-4-(3-piperidinemethyl)-thieno[2,3-d]pyridazinyl-7-formamide hydrochloride (100 mg) is added to a single mouth flask, then addition of water (5 ml) and the sodium carbonate is dropped to pH=9~10, stirred for 30 min. The above mixture is extracted by ethyl acetate, washed with water, and evaporated under reduced pressure to remove solvent to obtain 2-(4-chlorophenyl)-4-(3-piperidinemethyl)-thieno[2,3-d]pyridazinyl-7-formamide (70 mg).

EXAMPLE 2

2-(4-chlorophenyl)-4-(3-tetrahydropyranmethyl)-thieno[2,3-d]pyridazinyl-7-formamide

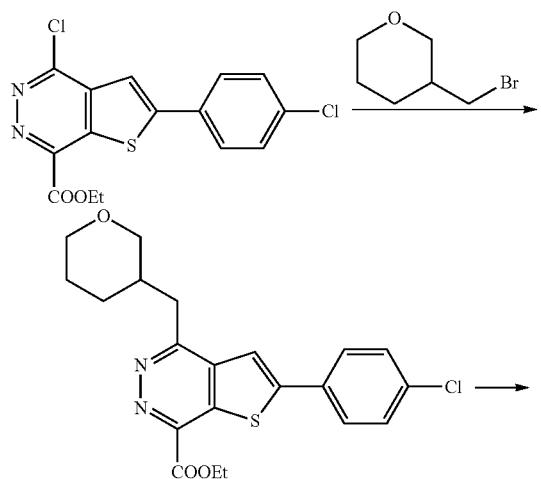

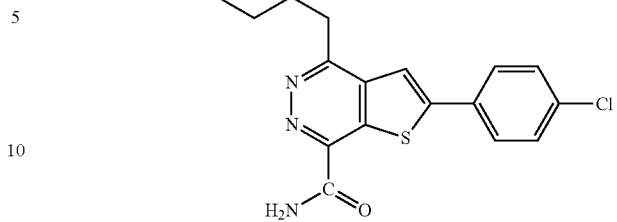

Step 1:

DMPU (225 ml), FeCl₃ (0.75 g) and CuCl (0.3 g) are added to 3-bromomethyltetrahydropyran (24.75 g, 0.138 mol), and then Et₂Zn (106.8 ml) is slowly dropped at 40~45° C. for 45 minutes to obtain a zinc-reagent.

THF (810 ml) and PdCl₂(dppf) (5.09 g) are added to 4-chloro-2-(4-chlorophenyl)-thieno[2,3-d]pyridazinyl-7-ethyl formate (30 g), and then addition of the zinc-reagent to the THF solution and reacted at 45° C. for 4 hours. The above mixture is poured into a saturated brine, filtrated after stiffing for 15 minutes and placed for layer separation. The aqueous phase is extracted with THF (500 ml, 2 times). The organic phase is combined together, washed with saturated brine (500 ml, 3 times) and dried with anhydrous Na₂SO₄ and evaporated under reduced pressure to remove solvent to obtain 4-(3-tetrahydropyranmethyl)-2-(4-chlorophenyl)-thieno[2,3-d]pyridazinyl-7-ethyl formate (25 g).

MS (ESI): 417 (M+1)

Step 2:

4-(3-tetrahydropyranmethyl)-2-(4-chlorophenyl)-thieno[2,3-d]pyridazinyl-7-ethyl formate (3 g), 1,4-dioxane (5 ml) and NH₃·H₂O (5 ml) are added to a sealed tube (25 ml) and heated at 80° C. over night, cooled to room temperature over night and transferred to a separating funnel next day, and addition of ethyl acetate, vibrated, placed for layer separation. The aqueous layer is reextracted with ethyl acetate for 2 times. The organic phase is combined together and adjusted with 1M HCl solution to pH≈3, then washed with a saturated brine to pH=7, dried with anhydrous Na₂SO₄ and filtered. The filtered liquid is purified with silica gel by chromatography to obtain a solid of 2-(4-chlorophenyl)-4-(3-tetrahydropyranmethyl)-thieno[2,3-d]pyridazinyl-7-formamide (2 g).

MS (ESI): 388 (M+1)

EXAMPLE 3

2-(4-chlorophenyl)-4-(3-tetrahydrothiapyranmethyl)-thieno[2,3-d]pyridazinyl-7-formamide

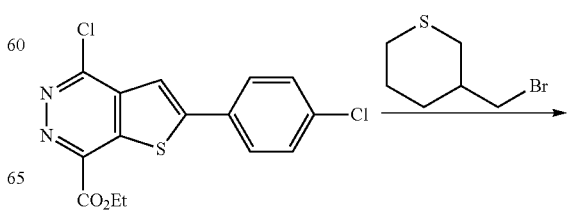

39

-continued

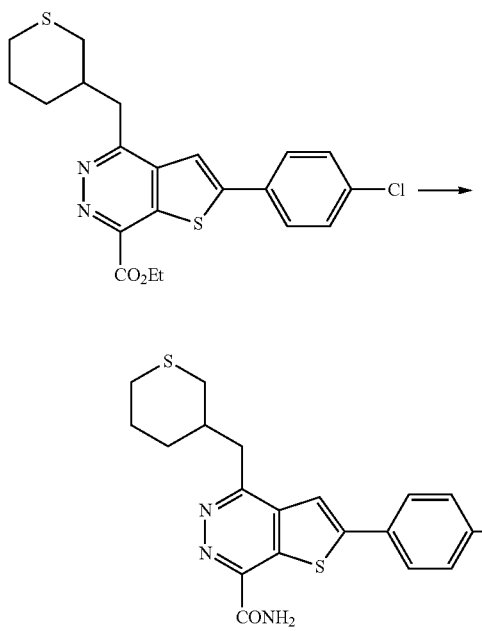

Step 1:

DMPU (225 ml), FeCl₃ (0.75 g) and CuCl (0.3 g) are added to 3-bromomethyl tetrahydrothiapyran (24.75 g, 0.138 mol), and then Et₂Zn (106.8 ml) is slowly added at 40~45° C. for 45 minutes to obtain a zinc-reagent.

THF (810 ml) and PdCl₂(dppf) (5.09 g) are added to 4-chloro-2-(4-chlorophenyl)-thieno[2,3-d]pyridazinyl-7-ethyl formate (30 g), and then the zinc-reagent is dropped to the THF solution at 45° C. for 4 hours. The reaction mixture is poured into a saturated brine, filtrated after stiffing for 15 minutes and placed for layer separation. The aqueous phase is extracted with THF (500 ml, 2 times). The organic phase is combined together, washed with a saturated brine (500 ml, 3 times) and dried with anhydrous Na₂SO₄ and evaporated under reduced pressure to remove solvent to obtain 4-(3-tetrahydropyranmethyl)-2-(4-chlorophenyl)-thieno[2,3-d]pyridazinyl-7-ethyl formate (25 g).

MS (ESI): 433 (M+1)

Step 2:

4-(3-tetrahydropyranmethyl)-2-(4-chlorophenyl)-thieno[2,3-d]pyridazinyl-7-ethyl formate (3 g), 1,4-dioxane (5 ml) and NH₃.H₂O (5 ml) are added to a sealed tube (25 ml) and heated at 80° C. over night, and cooled to room temperature and transferred to a separating funnel next day, and addition of ethyl acetate, vibrated, placed for layer separation. The aqueous layer is reextracted with ethyl acetate for 2 times. The organic phase is combined together and adjusted with 1M HCl solution to pH≈3, then washed with a saturated brine to pH=7, dried with anhydrous Na₂SO₄ and filtered. The filtered liquid is purified with silica gel by chromatography to obtain a solid of 2-(4-chlorophenyl)-4-(3-tetrahydropyranmethy)-thieno[2,3-d]pyridazinyl-7-formamide (2 g).

MS (ESI): 404 (M+1)

40

EXAMPLE 4

2-(4-chlorophenyl)-4-(2-piperidinemethyl)-thieno[2,3-d]pyridazinyl-7-formamide

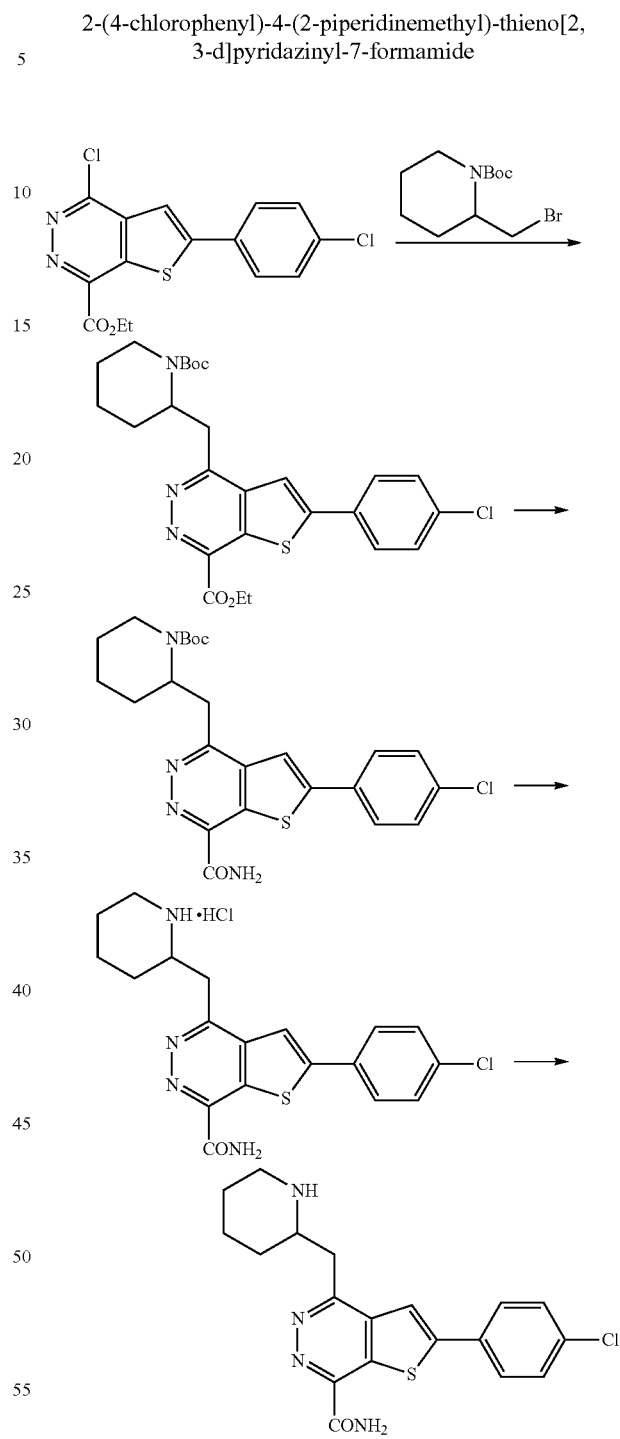

Step 1:

DMPU (225 ml), FeCl₃ (0.75 g) and CuCl (0.3 g) are added to N-Boc-2-bromomethyl piperidine (24.75 g, 0.138 mol), and then Et₂Zn (106.8 ml) is slowly added at 40~45° C. for 45 minutes to obtain a zinc-reagent.

THF (810 ml) and PdCl₂(dppf) (5.09 g) are added to 4-chloro-2-(4-chlorophenyl)-thieno[2,3-d]pyridazinyl-7-ethyl formate (30 g), and then the zinc-reagent is added to the THF solution at 45° C. for 4 hours. The reaction mixture is poured into a saturated brine, filtrated after stirring for 15 minutes and placed for layer separation. The aqueous phase is extracted with THF (500 ml, 2 times). The organic phase is combined together, washed with saturated brine (500 ml, 3 times) and dried with anhydrous $Na_2SO_4$ and evaporated under reduced pressure to remove solvent to obtain 2-(4-chlorophenyl)-4-(N-Boc-2-piperidinemethyl)-thieno[2,3-d]pyridazinyl-7-ethyl formate (25 g).

MS (ESI): 516 (M+1)

Step 2:

2-(4-chlorophenyl)-4-(N-Boc-2-piperidinemethyl)-thieno[2,3-d]pyridazinyl-7-ethyl formate (3 g), 1,4-dioxane (5 ml) and $NH_3 \cdot H_2O$ (5 ml) are added to a sealed tube (25 ml) and heated at 80° C. over night. The reaction mixture is cooled to room temperature and transferred into a separating funnel next day, and addition of ethyl acetate, vibrated, placed for layer separation. The water layer is reextracted with ethyl acetate for 2 times, the organic phase is combined together and adjusted to pH≈3 with 1M HCl solution, and then washed with a saturated brine to pH=7, dried with anhydrous $Na_2SO_4$ and filtered. The filtered liquid is purified with silica gel by chromatography to obtain a solid of 2(4-chlorophenyl)-4-(N-Boc-2-piperidinemethyl)-thieno[2,3-d]pyridazinyl-7-formamide (2 g).

MS (ESI): 487 (M+1)

Step 3:

4-(N-Boc-2-piperidinemethyl)-2(4-chlorophenyl)-7-aminocarbonyl-thieno[2,3-d]pyridazine (200 mg) and ethyl acetate (4 ml) are added to a single mouth flask (25 ml) and dissolved to a light yellow transparent solution. HCl solution (4 ml, 3M) is added and changed to a white suspension, heated at 30° C. for 1 h and the white suspension is changed to transparent. The reaction is tracked by plate. After reaction, the solvent is evaporated under reduced pressure to remove solvent to obtain a solid of 2-(4-chlorophenyl)-4-(N-Boc-2-piperidinemethyl)-thieno[2,3-d]pyridazinyl-7-formamide hydrochloride (100 mg).

MS (ESI): 423 (M+1)

Step 4:

2-(4-chlorophenyl)-4-(N-Boc-2-piperidinemethyl)-thieno[2,3-d]pyridazinyl-7-formamide hydrochloride (100 mg) is added to a single mouth flask, then addition of water (5 ml) and the sodium carbonate is dropped to pH=9~10, stirred for 30 min. The above mixture is extracted by ethyl acetate, washed, and evaporated under reduced pressure to remove solvent to obtain 2-(4-chlorophenyl)-4-(2-piperidinemethyl)-thieno[2,3-d]pyridazinyl-7-formamide (70 mg).

MS (ESI): 387 (M+1)

EXAMPLE 5

2-(4-chlorophenyl)-4-(4-piperidinemethyl)-thieno[2,3-d]pyridazinyl-7-formamide

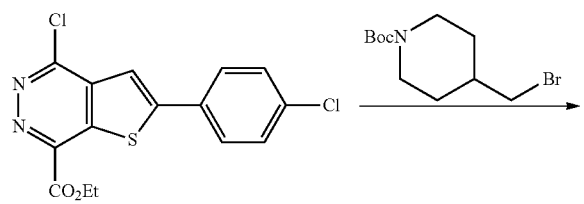

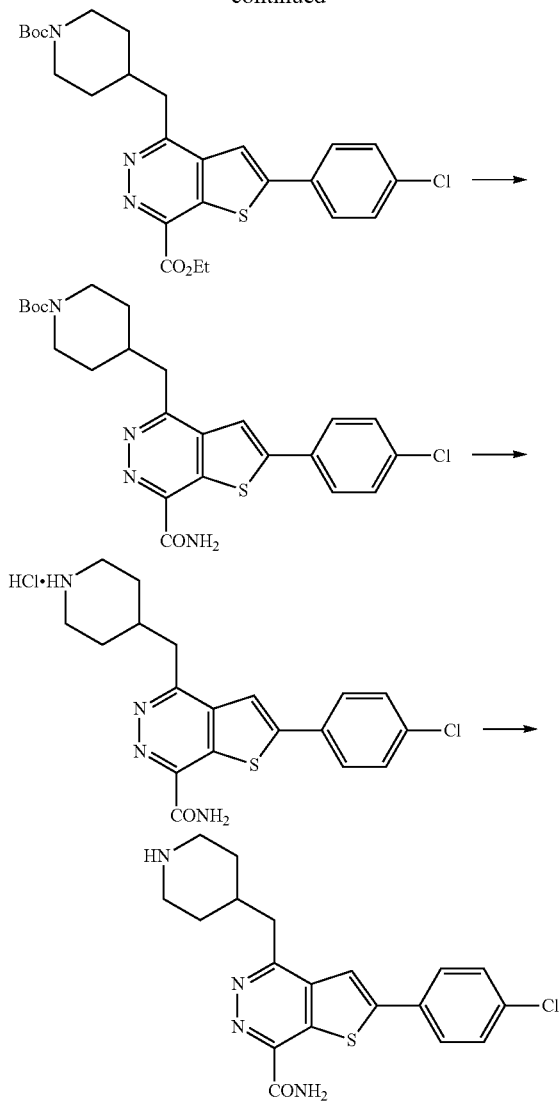

Step 1:

DMPU (225 ml), $FeCl_3$ (0.75 g) and CuCl (0.3 g) are added to N-Boc-4-bromomethylpiperidine (24.75 g, 0.138 mol), and then $Et_2Zn$ (106.8 ml) is slowly dropped at 40~45° C. for 45 minutes to obtain a zinc-reagent.

THF (810 ml) and $PdCl_2(dppf)$ (5.09 g) are added to 4-chloro-2-(4-chlorophenyl)-thieno[2,3-d]pyridazinyl-7-ethyl formate (30 g), and then the zinc-reagent is dropped to the THF solution at 45° C. for 4 h. The reaction mixture is poured into a saturated brine, filtrated after stirring for 15 minutes and placed for layer separation. The aqueous phase is extracted with THF (500 ml, 2 times). The organic phase is combined together, washed with a saturated brine (500 ml, 3 times) and dried with anhydrous $Na_2SO_4$, evaporated under reduced pressure to remove solvent to obtain 2-(4-chlorophenyl)-4-(N-Boc-4-piperidinemethyl)-thieno[2,3-d]pyridazinyl-7-ethyl formate (25 g).

MS (ESI): 515 (M+1)

Step 2:

2-(4-chlorophenyl)-4-(N-Boc-4-piperidinemethyl)-thieno[2,3-d]pyridazinyl-7-ethyl formate (3 g), 1,4-dioxane (5 ml) and $NH_3 \cdot H_2O$ (5 ml) are added to a sealed tube (25 ml) and heated at 80° C. over night. The reaction mixture is cooled to room temperature and transferred into a separating funnel next day, and addition of ethyl acetate, vibrated, placed for layer separation. The water layer is reextracted with ethyl acetate for 2 times, the organic phase is combined together and adjusted to pH≈3 with 1M HCl solution, and then washed with a saturated brine to pH=7, dried with anhydrous $Na_2SO_4$ and filtered. The filtered liquid is purified with silica gel by chromatography to obtain a solid of 2(4-chlorophenyl)-4-(N-Boc-4-piperidinemethyl)-thieno[2,3-d]pyridazinyl-7-formamide (2 g).

MS (ESI): 487 (M+1)

Step 3:

4-(N-Boc-4-piperidinemethyl)-2-(4-chlorophenyl)-7-aminocarbonyl-thieno[2,3-d]pyridazine (200 mg) and ethyl acetate (4 ml) are added to a single mouth flask (25 ml) and dissolved to a light yellow transparent solution. HCl solution (4 ml, 3M) is added and changed to a white suspension, heated at 30° C. for 1 h and the white suspension is changed to transparent. The reaction is tracked by plate. After reaction, the mixture is evaporated under reduced pressure to remove to obtain a solid of 2-(4-chlorophenyl)-4-(4-piperidinemethyl)-thieno[2,3-d]pyridazinyl-7-formamide hydrochloride (100 mg).

MS (ESI): 423 (M+1)

Step 4:

2-(4-chlorophenyl)-4-(4-piperidinemethyl)-thieno[2,3-d]pyridazinyl-7-formamide hydrochloride is added to a single mouth flask (25 ml), then water (5 ml) is added and the sodium carbonate is dropped to pH=9~10 stirred for 30 min. The above mixture is extracted by ethyl acetate, washed, and evaporated under reduced pressure to remove solvent to obtain 2-(4-chlorophenyl)-4-(4-piperidinemethyl)-thieno[2,3-d]pyridazinyl-7-formamide (70 mg).

MS (ESI): 387 (M+1)

EXAMPLE 6

2-(4-chlorophenyl)-4-(3-pyrrolidinemethyl)-thieno[2,3-d]pyridazinyl-7-formamide

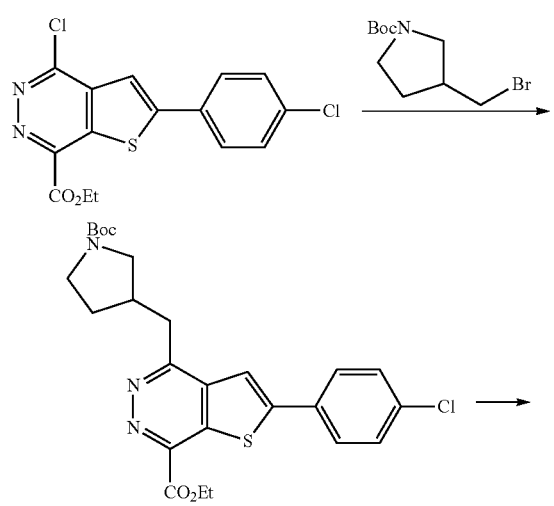

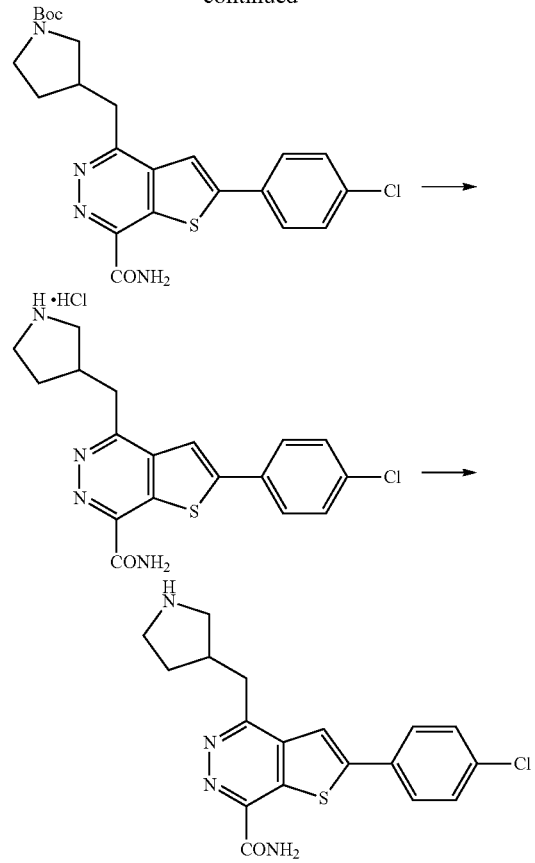

Step 1:

DMPU (225 ml), $FeCl_3$ (0.75 g) and CuCl (0.3 g) are added to N-Boc-3-bromomethylpyrrole (24.75 g, 0.138 mol), and then $Et_2Zn$ (106.8 ml) is slowly dropped at 40~45° C. for 45 minutes to obtain a zinc-reagent.

THF (810 ml) and $PdCl_2$(dppf) (5.09 g) are added to 4-chloro-2-(4-chlorophenyl)-thieno[2,3-d]pyridazinyl-7-ethyl formate (30 g), and then the zinc-reagent is added to the THF solution at 45° C. for 4 h. The reaction mixture is poured into a saturated brine, filtrated after stirring for 15 minutes and placed for layer separation. The aqueous phase is extracted with THF (500 ml, 2 times). The organic phase is combined together, washed with a saturated brine (500 ml, 3 times) and dried with anhydrous $Na_2SO_4$, ands evaporated under reduced pressure to remove solvent to obtain 2-(4-chlorophenyl)-4-(N-Boc-3-tetrahydropyrrolemethyl)-thieno[2,3-d]pyridazinyl-7-ethyl formate (25 g).

MS (ESI): 502 (M+1)

Step 2:

2-(4-chlorophenyl)-4-(N-Boc-3-tetrahydropyrrolemethyl)-thieno[2,3-d]pyridazinyl-7-ethyl formate (3 g), 1,4-dioxane (5 ml) and $NH_3.H_2O$ (5 ml) are added to a sealed tube (25 ml) and heated at 80° C. over night. The reaction liquid is cooled to room temperature and transferred into a separating funnel next day, and addition of ethyl acetate, vibrated, placed for layer separation. The water layer is reextracted with ethyl acetate for 2 times, the organic phase is combined together and adjusted to pH≈3 with 1M HCl solution, and then washed with a saturated brine to pH=7, dried with anhydrous $Na_2SO_4$ and filtered. The filtered liquid is purified with silica gel by chromatography to obtain a solid of 2(4-chlorophenyl)-4-(N-Boc-3-tetrahydropyrrole methyl)-thieno[2,3-d]pyridazinyl-7-formamide (2 g).

MS (ESI): 473 (M+1)

Step 3:

4-(N-Boc-3-tetrahydropyrrolemethyl)-2(4-chlorophenyl)-7-aminocarbonyl-thieno[2,3-d]pyridazine (200 mg) and ethyl acetate (4 ml) are added to a single mouth flask (25 ml) and dissolved to a light yellow transparent solution. HCl solution (4 ml, 3M) is added and changed to a white suspension, heated at 30° C. for 1 h and changed to transparent. The reaction is tracked by plate. After reaction, the solution is evaporated under reduced pressure to remove solvent to obtain a solid of 2-(4-chlorophenyl)-4-(3-tetrahydropyrrolemethyl)-thieno[2,3-d]pyridazinyl-7-formamide hydrochloride (100 mg).

MS (ESI): 409 (M+1)

Step 4:

2-(4-chlorophenyl)-4-(3-tetrahydropyrrolemethyl)-thieno[2,3-d]pyridazinyl-7-formamide hydrochloride is added to a single mouth flask (25 ml), then water (5 ml) is added and sodium carbonate is dropped to pH=9~10 and stirred for 30 min. The mixture is extracted by ethyl acetate, washed, and evaporated under reduced pressure to remove solvent to obtain 2-(4-chlorophenyl)-4-(3-tetrahydropyrrolemethyl)-thieno[2,3-d]pyridazinyl-7-formamide (70 mg).

MS (ESI): 373 (M+1)

EXAMPLE 7

2-(4-chlorophenyl)-4-(3-tetrahydrofuranmethyl)-thieno[2,3-d]pyridazinyl-7-formamide

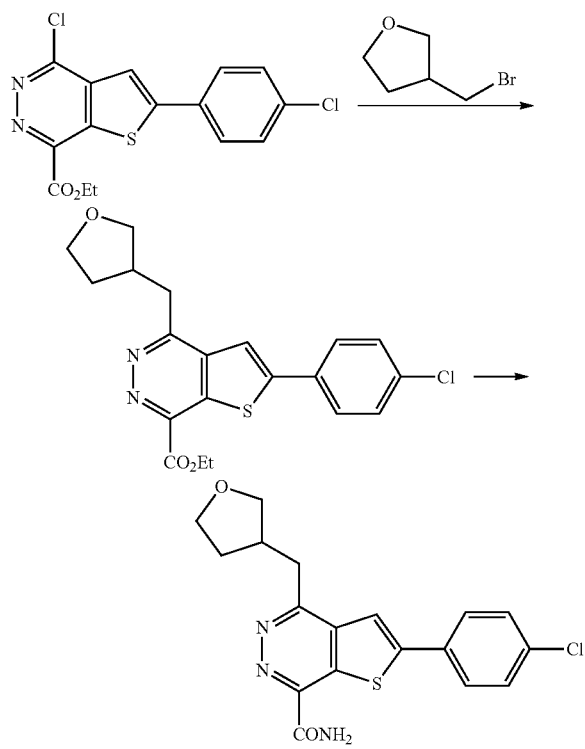

Step 1:

DMPU (225 ml), FeCl$_3$ (0.75 g) and CuCl (0.3 g) are added to 3-bromomethyltetrahydrofuran (24.75 g, 0.138 mol), and then Et$_2$Zn (106.8 ml) is slowly dropped at 40~45° C. for 45 minutes to obtain a zinc-reagent.

THF (810 ml) and PdCl$_2$(dppf) (5.09 g) are added to 4-chloro-2-(4-chlorophenyl)-thieno[2,3-d]pyridazinyl-7-ethyl formate (30 g), and then the zinc-reagent is dropped to the THF solution at 45° C. for 4 h. The reaction mixture is poured into a saturated brine, filtrated after stiffing for 15 minutes and placed for layer separation. The aqueous phase is extracted with THF (500 ml, 2 times). The organic phase is combined together, washed with a saturated brine (500 ml, 3 times) and dried with anhydrous Na$_2$SO$_4$, and evaporated under reduced pressure to remove solvent to obtain 4-(3-tetrahydropyranmethyl)-2-(4-chlorophenyl)-thieno[2,3-d]pyridazinyl-7-ethyl formate (25 g).

MS (ESI): 403 (M+1)

Step 2:

4-(3-tetrahydrofuranmethyl)-2-(4-chlorophenyl)-thieno[2,3-d]pyridazinyl-7-ethyl formate (3 g), 1,4-dioxane (5 ml) and NH$_3$.H$_2$O (5 ml) are added to a sealed tube (25 ml) and heated at 80° C. over night. The reaction is cooled to room temperature and transferred to a separating funnel next day, and addition of ethyl acetate, vibrated, placed for layer separation. The aqueous layer is reextracted with ethyl acetate for 2 times. The organic phase is combined together and adjusted with 1M HCl solution to pH≈3, then washed with saturated brine to pH=7, dried with anhydrous Na$_2$SO$_4$ and filtered. The filtered liquid is purified with silica gel by chromatography to obtain a solid of 2-(4-chlorophenyl)-4-(3-tetrahydrofuranmethyl)-thieno[2,3-d]pyridazinyl-7-formamide (2 g).

MS (ESI): 374 (M+1)

EXAMPLE 8

2-(4-chlorophenyl)-4-(3-tetrahydrothiophenemethyl)-thieno[2,3-d]pyridazinyl-7-formamide

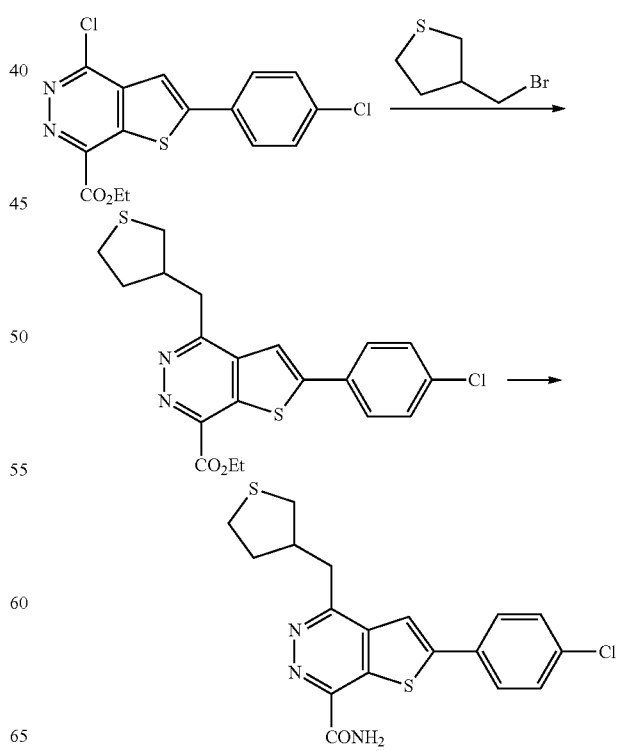

Step 1:

DMPU (225 ml), FeCl₃ (0.75 g) and CuCl (0.3 g) are added to 3-bromomethyl tetrahydrothiophene (24.75 g, 0.138 mol), and then Et₂Zn (106.8 ml) is slowly dropped at 40~45° C. for 45 minutes to obtain a zinc-reagent.

4-chloro-2-(4-chlorophenyl)-thieno[2,3-d]pyridazinyl-7-ethyl formate (30 g), THF (810 ml) and PdCl₂(dppf) (5.09 g) are added, and then the zinc-reagent is dropped to the THF solution at 45° C. for 4 h. The reaction mixture is poured into a saturated brine, filtrated after stirring for 15 minutes and placed for layer separation. The aqueous phase is extracted with THF (500 ml, 2 times). The organic phase is combined together, washed with a saturated brine (500 ml, 3 times) and dried with anhydrous Na₂SO₄, and evaporated under reduced pressure to remove solvent to obtain 4-(3-tetrahydrothiophenemethyl)-2-(4-chlorophenyl)-thieno[2,3-d]pyridazinyl-7-ethyl formate (25 g).

MS (ESI): 419 (M+1)

Step 2:

4-(3-tetrahydrothiophenemethyl)-2-(4-chlorophenyl)-thieno[2,3-d]pyridazinyl-7-ethyl formate (3 g), 1,4-dioxane (5 ml) and NH₃.H₂O (5 ml) are added to a sealed tube (25 ml) and heated at 80° C. over night. The reaction mixture is cooled to room temperature and transferred to a separating funnel next day, and addition of ethyl acetate, vibrated, placed for layer separation. The aqueous layer is reextracted with ethyl acetate for 2 times. The organic phase is combined together and adjusted with 1M HCl solution to pH≈3, then washed with a saturated brine to pH=7, dried with anhydrous Na₂SO₄ and filtered. The filtered liquid is purified with silica gel by chromatography to obtain a solid of 2-(4-chlorophenyl)-4-(3-tetrahydrothiophene methyl)-thieno[2,3-d]pyridazinyl-7-formamide (2 g).

MS (ESI): 389 (M+1)

EXAMPLE 9

2-(4-chlorophenyl)-4-(3-pyridinemethyl)-thieno[2,3-d]pyridazinyl-7-formamide

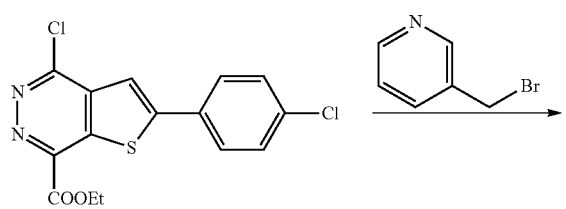

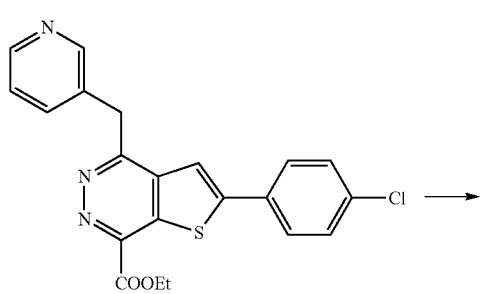

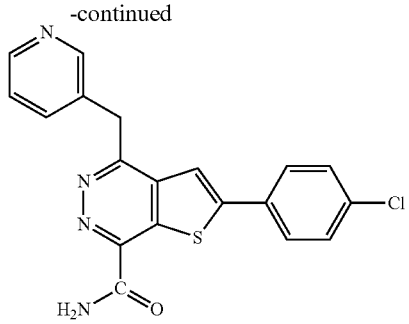

Step 1:

DMPU (225 ml), FeCl₃ (0.75 g) and CuCl (0.3 g) are added to 3-bromomethylpyridine (24.75 g, 0.138 mol), and then Et₂Zn (106.8 ml) is slowly dropped at 40~45° C. for 45 minutes to obtain a zinc-reagent.

THF (810 ml) and PdCl₂(dppf) (5.09 g) are added to 4-chloro-2-(4-chlorophenyl)-thieno[2,3-d]pyridazinyl-7-ethyl formate (30 g), and then the zinc-reagent is dropped to the THF solution at 45° C. for 4 h. The reaction mixture is poured into a saturated brine, filtered after stiffing for 15 minutes and placed for liquid separation. The aqueous phase is extracted with THF (500 ml, 2 times). The organic phase is combined together, washed with a saturated brine (500 ml, 3 times) and dried with anhydrous Na₂SO₄, and evaporated under reduced pressure to remove solvent to obtain 4-(3-pyridinemethyl)-2-(4-chlorophenyl)-thieno[2,3-d]pyridazinyl-7-ethyl formate (25 g).

MS (ESI): 410 (M+1)

Step 2:

4-(3-pyridinemethyl)-2-(4-chlorophenyl)-thieno[2,3-d]pyridazinyl-7-ethyl formate (3 g), 1,4-dioxane (5 ml) and NH3.H2O (5 ml) are added to a sealed tube (25 ml) and heated at 80° C. over night. The reaction mixture is cooled to room temperature and transferred to a separating funnel next day, and addition of ethyl acetate, vibrated, placed for layer separation. The aqueous layer is reextracted with ethyl acetate for 2 times. The organic phase is combined together and adjusted with 1M HCl solution to pH≈3, then washed with a saturated brine to pH=7, dried with anhydrous Na2SO4 and filtered. The filtered liquid is purified with silica gel by chromatography to obtain a solid of 2-(4-chlorophenyl)-4-(3-pyridinemethyl)-thieno[2,3-d]pyridazinyl-7-formamide (2 g).

MS (ESI): 381 (M+1)

EXAMPLE 10

2-(4-chlorophenyl)-4-(3-α-pyranmethyl)-thieno[2,3-d]pyridazinyl-7-formamide

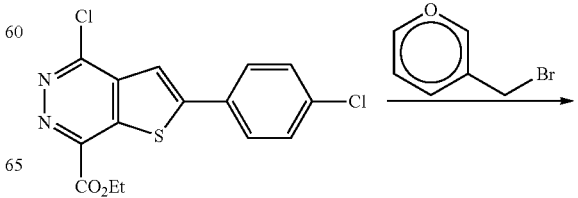

49
-continued

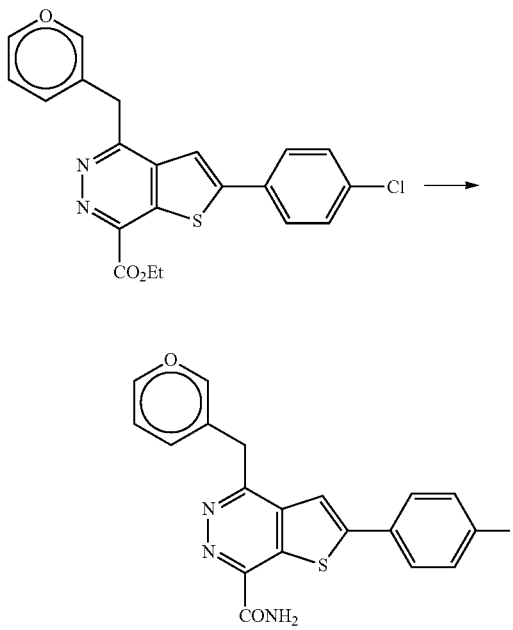

Step 1:

DMPU (225 ml), FeCl₃ (0.75 g) and CuCl (0.3 g) are added to 3-bromomethylpyran (24.75 g, 0.138 mol), and then Et₂Zn (106.8 ml) is slowly dropped at 40~45° C. for 45 minutes to obtain a zinc-reagent.

THF (810 ml) and PdCl₂(dppf) (5.09 g) are added to 4-chloro-2-(4-chlorophenyl)-thieno[2,3-d]pyridazinyl-7-ethyl formate (30 g), and then the zinc-reagent is dropped to the THF solution at 45° C. for 4 h. The reaction mixture is poured into a saturated brine, filtrated after stirring for 15 minutes and placed for layer separation. The aqueous phase is extracted with THF (500 ml, 2 times). The organic phase is combined together, washed with a saturated brine (500 ml, 3 times) and dried with anhydrous Na₂SO₄, and evaporated under reduced pressure to remove solvent to obtain 4-(3-α-pyranmethyl)-2-(4-chlorophenyl)-thieno[2,3-d]pyridazinyl-7-ethyl formate (25 g).

MS (ESI): 412 (M+1)

Step 2:

4-(3-α-pyranmethyl)-2-(4-chlorophenyl)-thieno[2,3-d]pyridazinyl-7-ethyl formate (3 g), 1,4-dioxane (5 ml) and NH₃.H₂O (5 ml) are added to a sealed tube (25 ml) and heated at 80° C. over night. The reaction mixture is cooled to room temperature and transferred to a separating funnel next day, and addition of ethyl acetate, vibrated, placed for layer separation. The aqueous layer is reextracted with ethyl acetate for 2 times. The organic phase is combined together and adjusted with 1M HCl solution to pH≈3, then washed with a saturated brine to pH=7, dried with anhydrous Na₂SO₄ and filtered. The filtered liquid is purified with silica gel by chromatography to obtain a solid of 2-(4-chlorophenyl)-4-(3-α-pyranmethyl)-thieno[2,3-d]pyridazinyl-7-formamide (2 g).

MS (ESI): 383 (M+1)

50
EXAMPLE 11

2-(4-chlorophenyl)-4-(3-α-thiapyranmethyl)-thieno[2,3-d]pyridazinyl-7-formamide

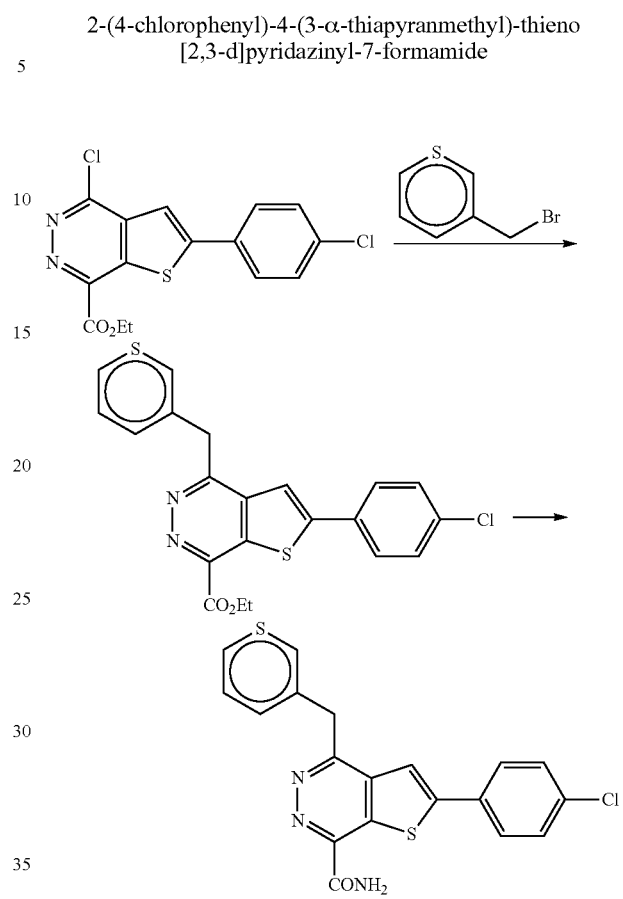

Step 1:

DMPU (225 ml), FeCl₃ (0.75 g) and CuCl (0.3 g) are added to 3-bromomethylthiopyran (24.75 g, 0.138 mol), and then Et₂Zn (106.8 ml) is slowly dropped at 40~45° C. for 45 minutes to obtain a zinc-reagent.

THF (810 ml) and PdCl₂(dppf) (5.09 g) are added to 4-chloro-2-(4-chlorophenyl)-thieno[2,3-d]pyridazinyl-7-ethyl formate (30 g), and then the zinc-reagent is dropped to the THF solution at 45° C. for 4 h. The reaction mixture is poured into a saturated brine, filtrated after stiffing for 15 minutes and placed for layer separation. The aqueous phase is extracted with THF (500 ml, 2 times). The organic phase is combined together, washed with a saturated brine (500 ml, 3 times) and dried with anhydrous Na₂SO₄, and evaporated under reduced pressure to remove solvent to obtain 4-(3-α-thiopyranmethyl)-2-(4-chlorophenyl)-thieno[2,3-d]pyridazinyl-7-ethyl formate (25 g).

MS (ESI): 428 (M+1)

Step 2:

4-(3-α-thiopyranmethyl)-2-(4-chlorophenyl)-thieno[2,3-d]pyridazinyl-7-ethyl formate (3 g), 1,4-dioxane (5 ml) and NH₃.H₂O (5 ml) are added to a sealed tube (25 ml) and heated at 80° C. over night. The reaction mixture is cooled to room temperature and transferred to a separating funnel next day, and addition of ethyl acetate, vibrated, placed for layer separation. The aqueous layer is reextracted with ethyl acetate for 2 times. The organic phase is combined and adjusted with 1M HCl solution to pH≈3, then washed with a saturated brine to pH=7, dried with anhydrous Na₂SO₄ and filtered. The filtered liquid is purified with silica gel by chromatography to obtain a solid of 2-(4-chlorophenyl)-4-(3-α-thiopyranmethyl)-thieno[2,3-d]pyridazinyl-7-formamide (2 g).

MS (ESI): 399 (M+1)

EXAMPLE 12

2-(4-chlorophenyl)-4-(2-pyridinemethyl)-thieno[2,3-d]pyridazinyl-7-formamide

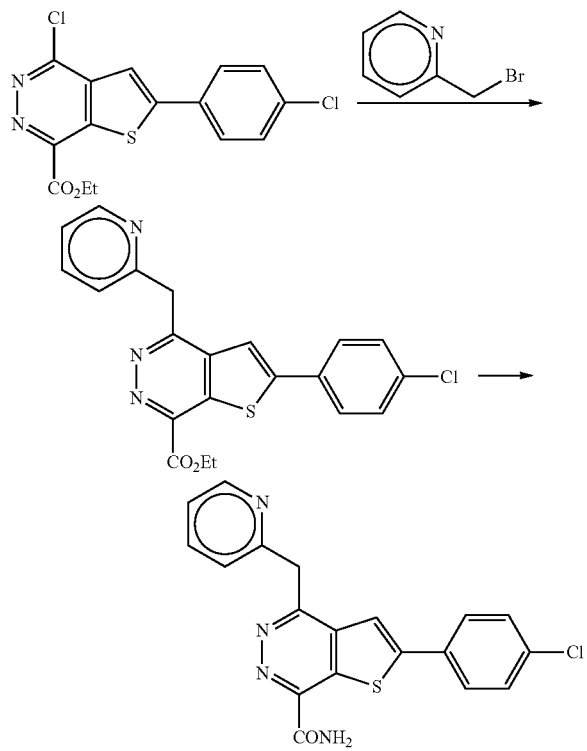

Step 1:

DMPU (225 ml), FeCl₃ (0.75 g) and CuCl (0.3 g) are added to 2-bromomethylpyridine (24.75 g, 0.138 mol), and then Et₂Zn (106.8 ml) is slowly dropped at 40~45° C. for 45 minutes to obtain a zinc-reagent.

THF (810 ml) and PdCl₂(dppf) (5.09 g) are added to 4-chloro-2-(4-chlorophenyl)-thieno[2,3-d]pyridazinyl-7-ethyl formate (30 g), and then the zinc-reagent is dropped to the THF solution at 45° C. for 4 hours. The reaction mixture is poured into a saturated brine, filtrated after stiffing for 15 minutes, and placed for layer separation. The aqueous phase is extracted with THF (500 ml, 2 times). The organic phase is combined together, washed with a saturated brine (500 ml, 3 times) and dried with anhydrous Na₂SO₄, and evaporated under reduced pressure to remove solvent to obtain 4-(2-pyridinemethyl)-2-(4-chlorophenyl)-thieno[2,3-d]pyridazinyl-7-ethyl formate (25 g).

MS (ESI): 410 (M+1)

Step 2:

4-(2-pyridinemethy)-2-(4-chlorophenyl)-thieno[2,3-d]pyridazinyl-7-ethyl formate (3 g), 1,4-dioxane (5 ml) and NH₃.H₂O (5 ml) are added to a sealed tube (25 ml) and heated at 80° C. over night. The reaction mixture is cooled to room temperature and transferred to a separating funnel next day, and addition of ethyl acetate, vibrated, placed for layer separation. The aqueous layer is reextracted with ethyl acetate for 2 times. The organic phase is combined together and adjusted with 1M HCl solution to pH≈3, then washed with a saturated brine to pH=7, dried with anhydrous Na2SO4 and filtered. The filtered liquid is purified with silica gel by chromatography to obtain a solid of 2-(4-chlorophenyl)-4-(2-pyridinemethyl)-thieno[2,3-d]pyridazinyl-7-formamide (2 g).

MS (ESI): 381 (M+1)

EXAMPLE 13

2-(4-chlorophenyl)-4-(4-pyridinemethyl)-thieno[2,3-d]pyridazinyl-7-formamide

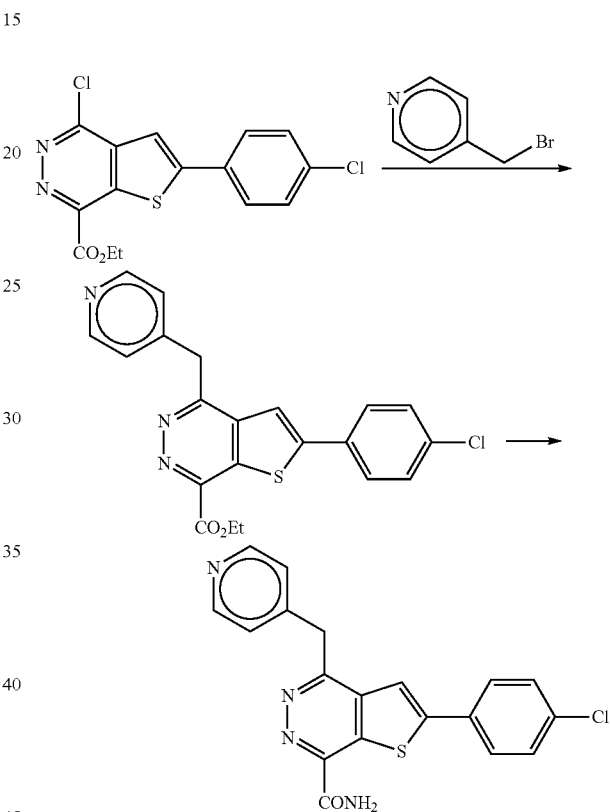

Step 1:

DMPU (225 ml), FeCl₃ (0.75 g) and CuCl (0.3 g) are added to 4-bromomethylpyridine (24.75 g, 0.138 mol), and then Et₂Zn (106.8 ml) is slowly dropped at 40~45° C. for 45 minutes to obtain a zinc-reagent.

THF (810 ml) and PdCl₂(dppf) (5.09 g) are added to 4-chloro-2-(4-chlorophenyl)-thieno[2,3-d]pyridazinyl-7-ethyl formate (30 g), and then the zinc-reagent is dropped to the THF solution at 45° C. for 4 h. The reaction mixture is poured into a saturated brine, filtrated after stiffing for 15 minutes and placed for layer separation. The aqueous phase is extracted with THF (500 ml, 2 times). The organic phase is combined together, washed with a saturated brine (500 ml, 3 times) and dried with anhydrous Na₂SO₄, ands evaporated under reduced pressure to remove solvent to obtain 4-(4-pyridinemethyl)-2-(4-chlorophenyl)-thieno[2,3-d]pyridazinyl-7-ethyl formate (25 g).

MS (ESI): 410 (M+1)

Step 2:

4-(4-pyridinemethyl)-2-(4-chlorophenyl)-thieno[2,3-d]pyridazinyl-7-ethyl formate (3 g), 1,4-dioxane (5 ml) and NH$_3$.H$_2$O (5 ml) are added to a sealed tube (25 ml) and heated at 80° C. over night. The reaction mixture is cooled to room temperature and transferred to a separating funnel next day, and addition of ethyl acetate, vibrated, placed for layer separation. The aqueous layer is reextracted with ethyl acetate for 2 times. The organic phase is combined together and adjusted with 1M HCl solution to pH≈3, then washed with saturated brine to pH=7, dried with anhydrous Na$_2$SO$_4$ and filtered. The filtered liquid is purified with silica gel by chromatography to obtain a solid of 2-(4-chlorophenyl)-4-(4-pyridinemethyl)-thieno[2,3-d]pyridazinyl-7-formamide (2 g).

MS (ESI): 381 (M+1)

EXAMPLE 14

2-(4-chlorophenyl)-4-(3-pyrrolemethyl)-thieno[2,3-d]pyridazinyl-7-formamide

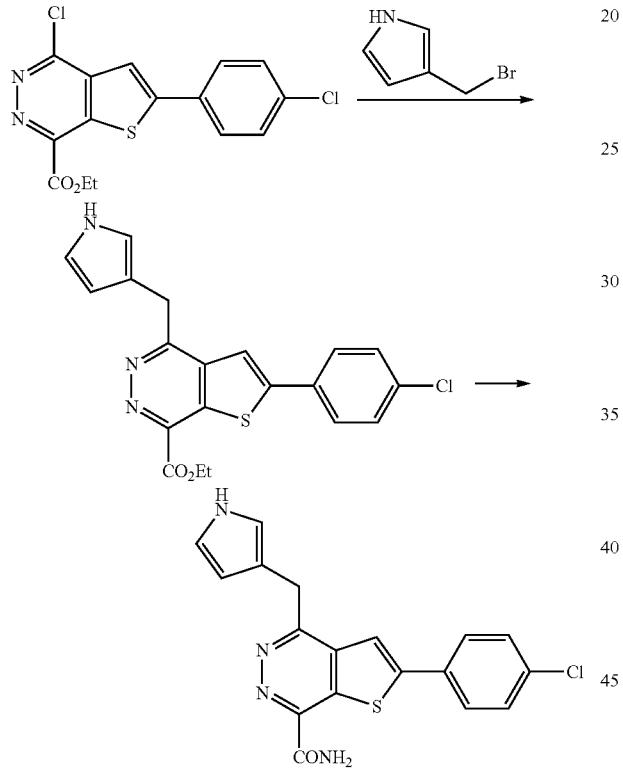

Step 1:

DMPU (225 ml), FeCl$_3$ (0.75 g) and CuCl (0.3 g) are added to 3-bromomethylpyrrole (24.75 g, 0.138 mol), and then Et$_2$Zn (106.8 ml) is slowly dropped at 40~45° C. for 45 minutes to obtain a zinc-reagent.

THF (810 ml) and PdCl$_2$(dppf) (5.09 g) are added to 4-chloro-2-(4-chlorophenyl)-thieno[2,3-d]pyridazinyl-7-ethyl formate (30 g), and then the zinc-reagent is dropped to the THF solution at 45° C. for 4 h. The reaction mixture is poured into a saturated brine, filtrated after stirring for 15 minutes and placed for layer separation. The aqueous phase is extracted with THF (500 ml, 2 times). The organic phase is combined together, washed with a saturated brine (500 ml, 3 times) and dried with anhydrous Na$_2$SO$_4$, and evaporated under reduced pressure to remove solvent to obtain 4-(3-pyrrolemethyl)-2-(4-chlorophenyl)-thieno[2,3-d]pyridazinyl-7-ethyl formate (25 g).

MS (ESI): 398 (M+1)

Step 2:

4-(3-pyrrolemethyl)-2-(4-chlorophenyl)-thieno[2,3-d]pyridazinyl-7-ethyl formate (3 g), 1,4-dioxane (5 ml) and NH$_3$.H$_2$O (5 ml) are added to a sealed tube (25 ml) and heated at 80° C. over night. The reaction mixture is cooled to room temperature and transferred to a separating funnel next day, and addition of ethyl acetate, vibrated, placed for layer separation. The aqueous layer is reextracted with ethyl acetate for 2 times. The organic phase is combined together and adjusted with 1M HCl solution to pH≈3, then washed with a saturated brine to pH=7, dried with anhydrous Na$_2$SO$_4$ and filtered. The filtered liquid is purified with silica gel by chromatography to obtain a solid of 2-(4-chlorophenyl)-4-(3-pyrrolemethyl)-thieno[2,3-d]pyridazinyl-7-formamide (2 g).

MS (ESI): 369 (M+1)

EXAMPLE 15

2-(4-chlorophenyl)-4-(3-furanmethyl)-thieno[2,3-d]pyridazinyl-7-formamide

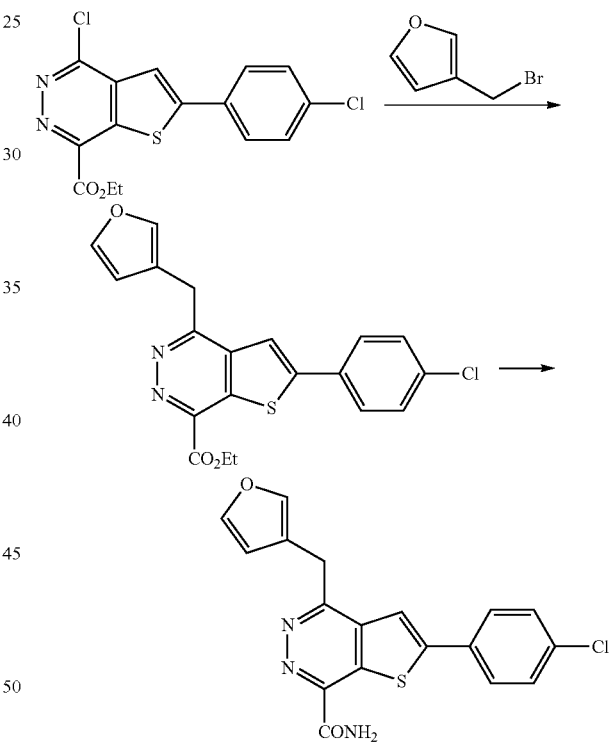

Step 1:

DMPU (225 ml), FeCl$_3$ (0.75 g) and CuCl (0.3 g) are added to 3-bromomethylfuran (24.75 g, 0.138 mol), and then Et$_2$Zn (106.8 ml) is slowly dropped at 40~45° C. for 45 minutes to obtain a zinc-reagent.

THF (810 ml) and PdCl$_2$(dppf) (5.09 g) are added to 4-chloro-2-(4-chlorophenyl)-thieno[2,3-d]pyridazinyl-7-ethyl formate (30 g), and then the zinc-reagent is added dropwise to the THF solution at 45° C. for 4 h. The reaction mixture is poured into a saturated brine, filtrated after stirring for 15 minutes and place for layer separation. The aqueous phase is extracted with THF (500 ml, 2 times). The organic phase is combined together, washed with a saturated brine (500 ml, 3 times) and dried with anhydrous Na$_2$SO$_4$, and evaporated under reduced pressure to remove solvent to obtain 4-(3-furanmethyl)-2-(4-chlorophenyl)-thieno[2,3-d]pyridazinyl-7-ethyl formate (25 g).

MS (ESI): 399 (M+1)

Step 2:

4-(3-furanmethyl)-2-(4-chlorophenyl)-thieno[2,3-d]pyridazinyl-7-ethyl formate (3 g), 1,4-dioxane (5 ml) and NH$_3$.H$_2$O (5 ml) are added to a sealed tube (25 ml) and heated at 80° C. over night. The reaction mixture is cooled to room temperature and transferred to a separating funnel next day, and addition of ethyl acetate, vibrated, placed for layer separation. The aqueous layer is reextracted with ethyl acetate for 2 times. The organic phase is combined together and adjusted with 1M HCl solution to pH≈3, then washed with a saturated brine to pH=7, dried with anhydrous Na$_2$SO$_4$ and filtered. The filtered liquid is purified with silica gel by chromatography to obtain a solid of 2-(4-chlorophenyl)-4-(3-furanmethyl)-thieno[2,3-d]pyridazinyl-7-formamide (2 g).

MS (ESI): 370 (M+1)

EXAMPLE 16

2-(4-chlorophenyl)-4-(3-thiaphenemethyl)-thieno[2,3-d]pyridazinyl-7-formamide

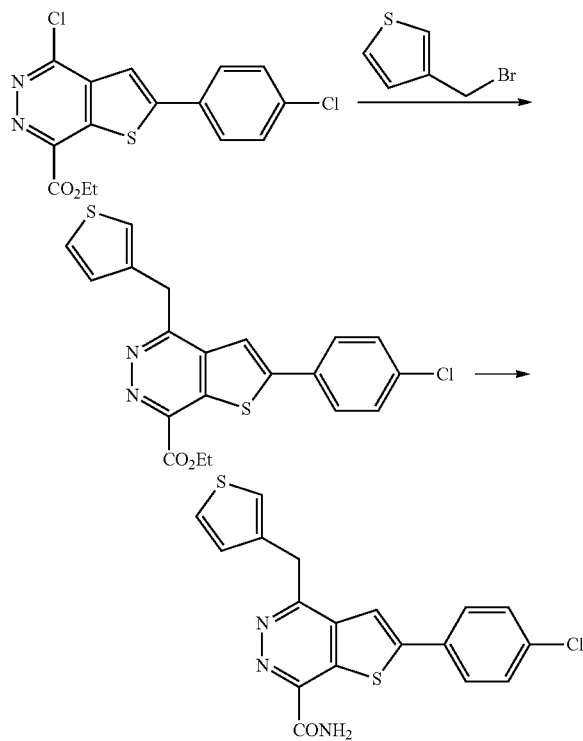

Step 1:

DMPU (225 ml), FeCl$_3$ (0.75 g) and CuCl (0.3 g) are added to 3-bromomethylthiophene (24.75 g, 0.138 mol), and then Et$_2$Zn (106.8 ml) is slowly dropped at 40~45° C. for 45 minutes to obtain a zinc-reagent.

THF (810 ml) and PdCl$_2$(dppf) (5.09 g) are added to 4-chloro-2-(4-chlorophenyl)-thieno[2,3-d]pyridazinyl-7-ethyl formate (30 g), and then the zinc-reagent is dropped to the THF solution at 45° C. for 4 h. The reaction mixture is poured into a saturated brine, filtrated after stirring for 15 minutes and placed for layer separation. The aqueous phase is extracted with THF (500 ml, 2 times). The organic phase is combined together, washed with a saturated brine (500 ml, 3 times) and dried with anhydrous Na$_2$SO$_4$, and evaporated under reduced pressure to remove solvent to obtain 4-(3-thiophenemethyl)-2-(4-chlorophenyl)-thieno[2,3-d]pyridazinyl-7-ethyl formate (25 g).

MS (ESI): 415 (M+1)

Step 2:

4-(3-thiophenemethyl)-2-(4-chlorophenyl)-thieno[2,3-d]pyridazinyl-7-ethyl formate (3 g), 1,4-dioxane (5 ml) and NH$_3$.H$_2$O (5 ml) are added to a sealed tube (25 ml) and heated at 80° C. over night. The reaction mixture is cooled to room temperature and transferred to a separating funnel next day, and addition of ethyl acetate, vibrated, placed for layer separation. The aqueous layer is reextracted with ethyl acetate for 2 times. The organic phase is combined together and adjusted with 1M HCl solution to pH≈3, then washed with a saturated brine to pH=7, dried with anhydrous Na$_2$SO$_4$ and filtered. The filtered liquid is purified with silica gel by chromatography to obtain a solid of 2-(4-chlorophenyl)-4-(3-thiophenemethyl)-thieno[2,3-d]pyridazinyl-7-formamide (2 g).

MS (ESI): 386 (M+1)

EXAMPLE 17

2-(4-chlorophenyl)-4-(2-pyrrolemethyl)-thieno[2,3-d]pyridazinyl-7-formamide

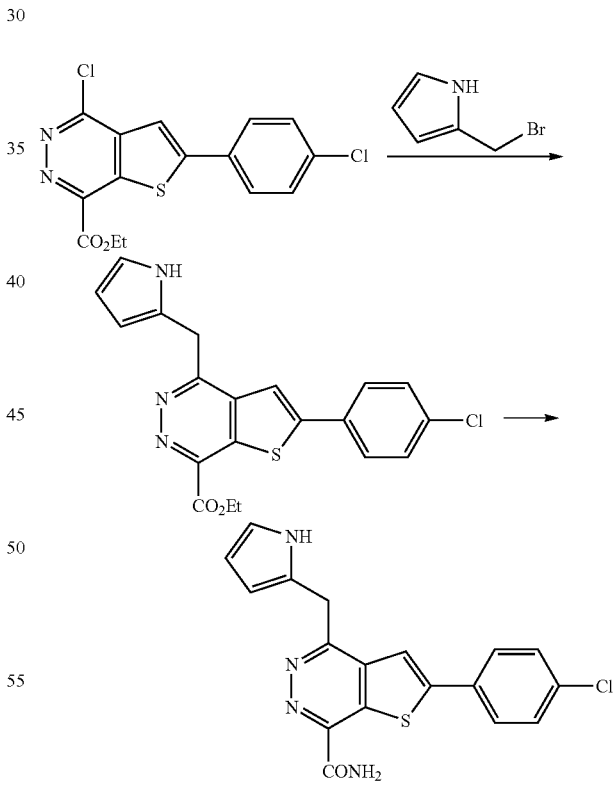

Step 1:

DMPU (225 ml), FeCl$_3$ (0.75 g) and CuCl (0.3 g) are added to 2-bromomethylpyrrole (24.75 g, 0.138 mol), and then Et$_2$Zn (106.8 ml) is slowly dropped at 40~45° C. for 45 minutes to obtain a zinc-reagent.

THF (810 ml) and PdCl$_2$(dppf) (5.09 g) are added to 4-chloro-2-(4-chlorophenyl)-thieno[2,3-d]pyridazinyl-7- ethyl formate (30 g), and then the zinc-reagent is dropped to the THF solution at 45° C. for 4 h. The reaction mixture is poured into a saturated brine, filtrated after stirring for 15 minutes and placed for layer separation. The aqueous phase is extracted with THF (500 ml, 2 times). The organic phase is combined together, washed with a saturated brine (500 ml, 3 times) and dried with anhydrous $Na_2SO_4$, and evaporated under reduced pressure to remove solvent to obtain 4-(2-pyrrolemethyl)-2-(4-chlorophenyl)-thieno[2,3-d]pyridazinyl-7-ethyl formate (25 g).

MS (ESI): 398 (M+1)

Step 2:

4-(2-pyrrolemethyl)-2-(4-chlorophenyl)-thieno[2,3-d]pyridazinyl-7-ethyl formate (3 g), 1,4-dioxane (5 ml) and $NH_3 \cdot H_2O$ (5 ml) are added to a sealed tube (25 ml) and heated at 80° C. over night. The reaction mixture is cooled to room temperature and transferred to a separating funnel next day, and addition of ethyl acetate, vibrated, placed for layer separation. The aqueous layer is reextracted with ethyl acetate for 2 times. The organic phase is combined together and adjusted with 1M HCl solution to pH≈3, then washed with a saturated brine to pH=7, dried with anhydrous $Na_2SO_4$ and filtered. The filtered liquid is purified with silica gel by chromatography to obtain a solid of 2-(4-chlorophenyl)-4-(2-pyrrolemethyl)-thieno[2,3-d]pyridazinyl-7-formamide (2 g).

MS (ESI): 369 (M+1)

EXAMPLE 18

2-(3,5-dichlorophenyl)-4-(3-piperidinemethyl)-thieno[2,3-d]pyridazinyl-7-formamide

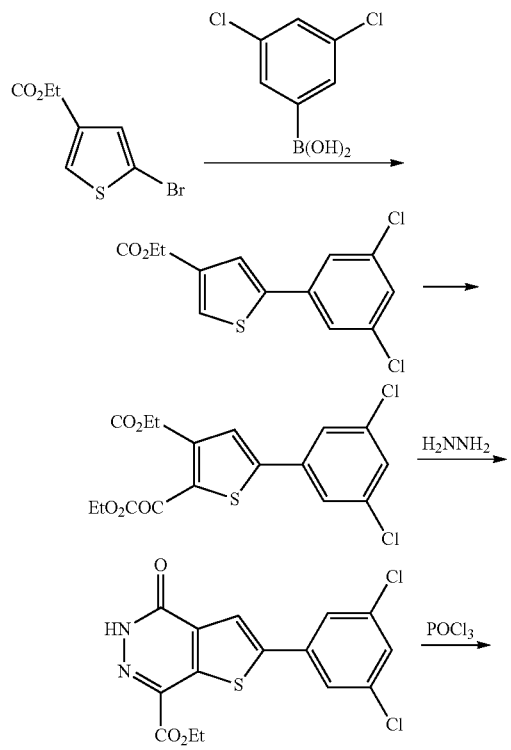

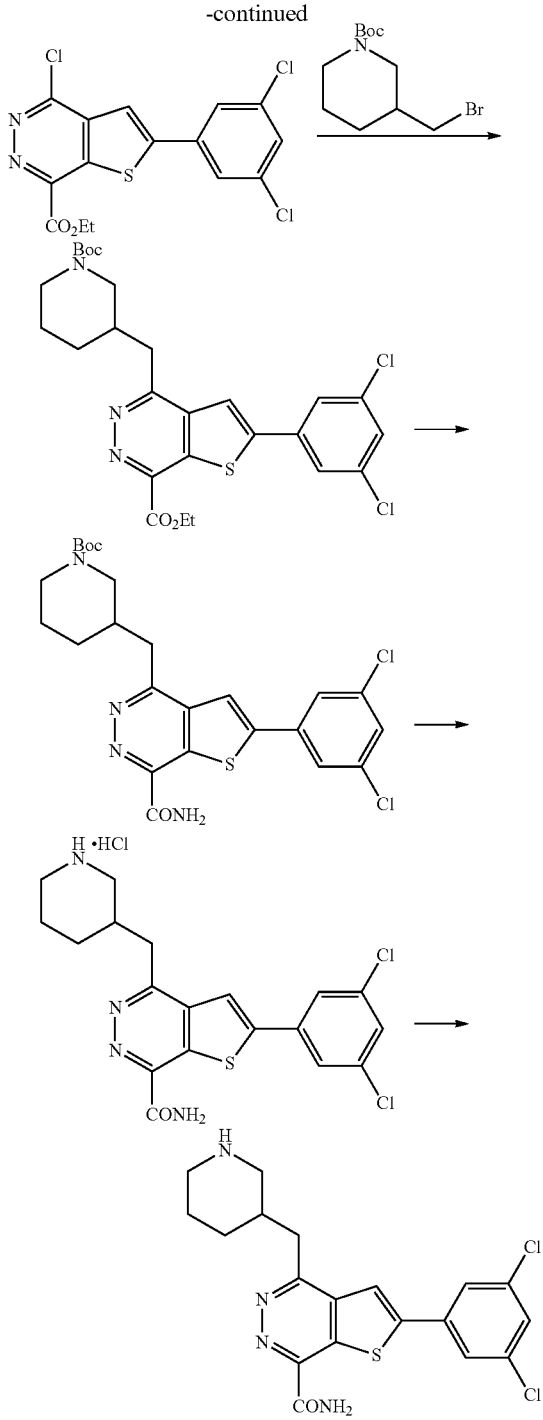

Step 1:

5-bromo-thiophene-3-ethyl formate (10.5 g), 3,5-dichlorobenzene boronic acid (6 g), $Pd[P(Ph)_3]_4$ (1.5 g), sodium carbonate (7.5 g) and a mixture (347 ml) of toluene:water: EtOH (4:2:1, v/v) are in turn added to a three mouth flask (500 ml) and heated at reflux for 3 h. The reaction is tracked by TLC. The reaction mixture is cooled to room temperature after reaction, and placed for layer separation. The aqueous phase is extracted with toluene (35 ml, 2 times). The organic phase is combined together and washed with a saturated brine to pH=7, dried with anhydrous sodium sulfate over night and filtered next day, and evaporated under reduced pressure to remove solvent to obtain a light yellow viscous fluid, placed for solid condensation, and recrystallized with absolute EtOH to obtain a crystal of 5-(3,5-dichlorophenyl)-3-thiophene-ethyl formate (8.6 g).

Step 2:

Preparation of LDA: THF (252.6 ml) and N,N-diisopropylamine (79 ml) are added into a three mouth flask (1000 ml) under argon, and n-BuLi (302.8 ml, 1.6M in hexane) is added into a constant pressure funnel (500 ml) and is dropped when the inner temperature is below −20° C. with an intensely exothermic reaction, and kept the inner temperature between −20° C.~−30° C. by controlling a adding speed. After addition, the reaction mixture is naturally warmed up to room temperature, and then directly used for the following condensation reaction.

Condensation Reaction: 5-(3,5-dichlorophenyl)thiophene-3-ethyl formate (28.7 g), THF (1084 ml) and diethyloxalate (29.7 ml) are added into a four mouth flask (2000 ml) connecting with a mechanical stiffing apparatus, a 500 ml constant pressure funnel and a temperature probe. The above mixture is stirred at room temperature and dissolved to obtain a light yellow transparent liquid. The LDA solution prepared is transferred into a constant pressure funnel under argon, cooled, and then the LDA is dropped into the flask when the inner temperature is below −78° C., and kept the inner temperature below −78° C. by controlling the adding speed. After addition, the reaction is tracked by TLC. HCl solution (2.2M) is added to adjust pH≈3 after reaction, and the color of the reaction mixture is changed from reddish brown into orange. The temperature is warmed up to about 0° C., a solid NaCl is then added, and desolved under stirring, and then placed for layer separation. The aqueous phase is reextracted with THF (143.5 ml, 2 times). The organic phase is combined together and washed with a saturated brine for two times, and then adjusted pH≈8 with diluted sodium carbonate solution; finally, washed with a saturated brine to pH=7, dried with anhydrous sodium sulfate, filtered and evaporated under reduced pressure to remove solvent to obtain a light yellow viscous fluid, placed at room temperature and gradually condensated to solid, recrystallized by EtOH to obtain a pure product of 5-(3,5-dichlorophenyl)-2-ethoxyoxalyl-thiophene-3-ethyl formate (orange crystal, 25.5 g).

Step 3:

A crystal of 5-(3,5-dichlorophenyl)-2-ethoxyoxalyl-thiophene-3-ethyl formate (3.0 g), and absolute ethanol (45 ml) are added into a reaction flask (100 ml), stirred at room temperature to obtain a yellow suspension. The hydrazine hydrate (0.75 ml) is added into a constant pressure funnel under stiffing for 10 minutes and then dropped to the flask. The yellow suspension is dissolved to a transparent liquid, and heated at 70° C. to gradually precipitate yellow solids in the flask with rise of the temperature, and the reaction liquid increasingly becomes viscous, and kept for 1 h and then cooled to room temperature, and filtered to obtain a pistachio solid, the solid is respectively washed with a mixture of hexane/dichloromethane (1:1)(15 ml, 2 times) and methanol/dichloromethane (1:1)(15 ml, 2 times) and dried under a reduced pressure to obtain 2-(3,5-dichlorophenyl)-4-oxo-4,5-dihydro-thieno[2,3-d]pyridazine-7-ethyl formate (2.75 g).

Step 4:

2-(3,5-dichlorophenyl)-4-oxo-4,5-dihydro-thieno[2,3-d]pyridazine-7-ethyl formate (1.5 g) and phosphorous oxychloride (22.5 ml) are added to a three mouth flask (100 ml), heated at 90° C. for 3 h, and gradually dissolved to obtain a dark red brown solution. After reaction, the solution is cooled to room temperature and evaporated under reduced pressure to remove solvent to obtain a chocolate brown viscous fluid. THF and a saturated brine are added under stirring, then yellow solids are precipitated, filtered, placed for layer separation, and reextracted and adjusted to pH≈9 with diluted sodium carbonate solution after the organic phase is combined, and then washed with a saturated brine to pH=7, and dried with anhydrous sodium sulfate, filtered, decolourised with active carbons at reflux to obtain a light yellow green liquid, the liquid is evaporated under reduced pressure to remove solvent to obtain 4-chloro-2-(3,5-dichlorophenyl)-thieno[2,3-d]pyridazinyl-7-ethyl formate (light green flocculent solid, 1.0 g).

Step 5:

DMPU (5 ml), FeCl$_3$ (0.017 g) and CuCl (0.007 g) are added to N-Boc-3-bromomethylpiperidine (0.55 g), and then Et$_2$Zn (2.5 ml) is slowly dropped at 40~45° C. for 45 minutes to obtain a zinc-reagent.

THF (18 ml) and PdCl$_2$(dppf) (0.12 g) are added to 4-chloro-2-(3,5-dichlorophenyl)-thieno[2,3-d]pyridazinyl-7-ethyl formate (30 g), and then the zinc-reagent is dropped to the THF solution at 45° C. for 4 h. The reaction mixture is poured into a saturated brine, filtrated after stirring for 15 minutes and placed for layer separation. The aqueous phase is extracted with THF (80 ml, 2 times). The organic phase is combined together, washed with a saturated brine (80 ml, 3 times) and dried with anhydrous Na$_2$SO$_4$, and evaporated under reduced pressure to remove solvent to obtain 2-(3,5-dichlorophenyl)-4-(N-Boc-3-piperidinemethyl)-thieno[2,3-d]pyridazinyl-7-ethyl formate (0.5 g).

Step 6:

2-(3,5-dichlorophenyl)-4-(N-Boc-3-piperidinemethyl)-thieno[2,3-d]pyridazinyl-7-ethyl formate (0.5 g), 1,4-dioxane (1.0 ml) and NH$_3$.H$_2$O (5 ml) are added to a sealed tube (5 ml) and heated at 80° C. over night. The reaction mixture is cooled to room temperature and transferred into a separating funnel next day, and addition of ethyl acetate, vibrated, placed for layer separation. The water layer is reextracted with ethyl acetate for 2 times. The organic phase is combined together and adjusted to pH≈3 with 1M HCl solution, and then washed with saturated brine to pH=7, dried with anhydrous sodium sulfate and filtered. The filtered liquid was purified together with silica gel by flash chromatography to obtain a solid of 2(3,5-dichlorophenyl)-4-(N-Boc-3-piperidinemethyl)-thieno[2,3-d]pyridazinyl-7-formamide (0.3 g).

Step 7:

2(3,5-dichlorophenyl)-4-(N-Boc-3-piperidinemethyl)-thieno[2,3-d]pyridazinyl-7-formamide (200 g) and ethyl acetate (4 ml) are added to a single mouth flask (25 ml) and dissolved to a light yellow transparent solution. HCl solution (4 ml, 3M) is added and changed to a white suspension, and heated at 30° C. for 1 h and the white suspension is changed to transparent. The reaction is tracked by plate; and evaporated under reduced pressure after reaction to remove solvent to obtain a solid of 2-(3,5-dichlorophenyl)-4-(3-piperidinemethyl)-thieno[2,3-d]pyridazinyl-7-formamide hydrochloride (100 mg).

Step 8:

2-(3,5-dichlorophenyl)-4-(3-piperidinemethyl)-thieno[2,3-d]pyridazinyl-7-formamide hydrochloride (100 mg) is added to a single mouth flask (25 ml), then addition of water (5 ml) and the sodium carbonate is dropped to pH=9~10 under stirring for 30 min. The mixture is extracted by ethyl acetate, washed with water, and evaporated under reduced pressure to remove solvent to obtain 2-(3,5-dichlorophenyl)-4-(3-piperidinemethyl)-thieno[2,3-d]pyridazinyl-7-formamide (70 mg).

MS (ESI): 421 (M+1)

EXAMPLE 19

Preparation of Pharmaceutical Formulations

1. Injection
(1) Formulation

| | |
|---|---|
| Compound II | 50 g |
| Sodium chloride | 2250 g |
| Water for injection | 250,000 ml |
| To make | 1,000 bottles |

(2) Preparation

The compound II is added into a tank according to the formulation, and water for injection (about 200,000 ml) is added and dissolved completely. Sodium chloride is then added according to the formation, and then continue to add sufficient quantity sodium chloride after completely dissolved. pH is adjusted to 4.0~5.0. Activated carbon (250 g) is added for 30 minutes before being removed with filter decarbonization. The mixture is then bottled in 250 ml/bottle after precision filtration with Titanium Rod. The injection is prepared after water sterilization at 115° C. for 30 minutes.

2. Tablets
(1) Formulation

| | |
|---|---|
| Compound XXXIII | 50 g |
| Starch | 160 g |
| Hydroxypropyl cellulose | 39 g |
| Polyvidone K30 (5%) | q.s. |
| Sodium carboxy methyl starch | 10.4 g |
| Magnesium stearate | 1.3 g |
| To make | 1000 tablets |

(2) Preparation

Compound XXXIII, starch and hydroxypropyl cellulose are added into a hopper of fluidbedgranulator, and warmed up to 38° C.~45° C. by opening the main air to premix the material for 5 minutes. Suitable polyvidone K30 (5%) water solution is nebulized to granulate, the material is controlled to 55° C.~60° C. and dried for 10 minutes, mixed with sodium carboxy methyl starch and magnesium stearate to tablet after granulation.

3. Capsules
(1) Formulation

| | |
|---|---|
| Compound XXXXIV | 50 g |
| Lactose | 194.4 g |
| Sodium carboxy methyl starch | 7.8 g |
| Colloidal silicon dioxide | 5.2 g |
| Magnesium stearate | 2.6 g |
| To make | 1000 capsules |

(2) Preparation

Compound XXXXIV, lactose, sodium carboxy methyl starch and colloidal silicon dioxide are added into a mixer according to the formulation and mixed for 60 minutes to make it homogeneous. Magnesium stearate is then added according to the formulation and mixed for 10 minutes, filled in a general Gelatin plastic shell.

Some of the above compounds are tested in vitro and in vivo for their antitumor activities. Among these tests, the cytotoxicity is tested in vitro using SRB and MTT methods for 72 h. The specific activity data is summarized in Table 1. The growth inhibition effect of the compound on mouse S180 sarcoma is summarized in Table 2. The efficacy of the compounds on treating transplanted tumor of human colon cancer HT-99 on nude mice is summarized in Table 3.

TABLE 1

Anti-cancer Activity of the Compound IC50(μM) In vitro

| Order No. | Compound No. | Human poorly differentiated gastric adenocarcinoma (BGC-823) | Human colon cancer HT-29 | Mouse lung cancer (3LL) | Human ovarian cancer (A2780) |
|---|---|---|---|---|---|
| 1 | I | 3.35 | 4.22 | 1.40 | 6.40 |
| 2 | II | 4.47 | 7.4 | 3.32 | 6.20 |
| 3 | VI | 5.86 | 7.53 | 2.55 | 1.54 |
| 4 | XI | 9.24 | 10.70 | 8.43 | 11.85 |
| 5 | XIII | 2.62 | 0.73 | 1.24 | 1.18 |
| 6 | XIV | 30.46 | 16.76 | 8.59 | 6.01 |
| 7 | XV | 2.25 | | 804 | |
| 8 | XXI | | 8.68 | | |
| 9 | XXIII | >100 | 5.57 | >100 | >100 |
| 10 | XXVI | 24.58 | >100 | >100 | >100 |
| 11 | XXXIV | 74.50 | >100 | 50.64 | >100 |
| 12 | XXXVIII | 8.17 | 1.33 | 3.13 | 3.13 |
| 13 | XXXXVI | 11.11 | >100 | >100 | 30.29 |
| 14 | XXXXXVIII | 16.4 | 21.8 | 21.4 | 13.9 |
| 15 | XXXXXXIX | 17.02 | 9.48 | 3.31 | 7.11 |
| 16 | XXXXXXX | 5.45 | >100 | >100 | >100 |

TABLE 2

The growth inhibition effects of the compounds on mouse S180 colon cancer
N = 7 –X ± SD

| Compound No. | Dosage mg/kg | Adimin Route | Starting Body Weight(g) | Ending Body Weight(g) | Tumor Weight (g) | Body Weight without Tumor (g) | Rate of inhibition (%) |
|---|---|---|---|---|---|---|---|
| II | 50 | ip | 19.70 ± 0.76 | 20.03 ± 1.11 | 1.41 ± 0.30 | 18.63 ± 0.93 | 52.62 |
| XX | 50 | ip. | 19.50 ± 0.89 | 21.19 ± 1.40 | 1.86 ± 0.26 | 19.33 ± 1.60 | 37.23 |

TABLE 2-continued

The growth inhibition effects of the compounds on mouse S180 colon cancer
N = 7 –X ± SD

| Compound No. | Dosage mg/kg | Adimin Route | Starting Body Weight(g) | Ending Body Weight(g) | Tumor Weight (g) | Body Weight without Tumor (g) | Rate of inhibition (%) |
|---|---|---|---|---|---|---|---|
| XII | 50 | ip. | 19.50 ± 0.73 | 20.79 ± 1.83 | 1.48 ± 0.16 | 19.31 ± 1.79 | 50.02 |
| XXIV | 50 | ip | 19.39 ± 0.60 | 23.18 ± 1.66 | 1.62 ± 0.26 | 21.56 ± 1.48 | 45.45 |
| Negative Control | | | 19.49 ± 0.76 | 26.21 ± 2.38 | 2.97 ± 0.63 | 23.24 ± 2.18 | |

Note:
ip: administration of intraperitoneal injection.

TABLE 3

The efficacy of the compound on treating transplanted tumor of human colon cancer HT-99 on nude mice

| Compound No. | Dosage mg/kg | Adimin. Route | No. of Animals d0/dn | TV(X + SD, mm$^3$) d0 | dn | RTV X ± SD | T/C (%) |
|---|---|---|---|---|---|---|---|
| II | 60 | ip, d0, 1 | 6/3 | 146 ± 13 | 690 ± 271 | 4.64 ± 1.65 | 70 |
| V | 60 | ip, d0, 1 | 6/3 | 150 ± 16 | 910 ± 0 | 6.40 ± 0 | 96.5 |
| XI | 60 | ip, d0, 1 | 6/1 | 150 ± 15 | 1224 ± 440 | 7.52 ± 0.26 | 113.4 |
| XIX | 60 | ip, d0, 1 | 6/3 | 147 ± 9 | 663 ± 86 | 4.53 ± 0.82 | 68.3 |
| XXII | 60 | ip, d0, 1 | 6/3 | 151 ± 11 | 714 ± 127 | 4.69 ± 0.71 | 70.7 |
| XXX | 60 | ip, d0, 1 | 6/3 | 144 ± 23 | 482 ± 83 | 3.78 ± 1.09 | 57.0 |
| XXXI | 60 | ip, d0, 1 | 6/3 | 145 ± 13 | 785 ± 300 | 5.36 ± 1.94 | 80.8 |
| GCT + II | 20 + 25 | ip + iv, d0, 1 | 6/6 | 183 ± 7 | 409 ± 81 | 1.58 ± 0.27 | 30 |
| GCT + XI | 20 + 25 | ip + iv, d0, 1 | 6/6 | 196 ± 15 | 399 ± 89 | 1.55 ± 0.22 | 27 |
| GCT | 20 | ip, d0, 1 | 6/6 | 184 ± 17 | 463 ± 74 | 1.64 ± 0.44 | 37 |
| CPT-11 + II | 20 + 25 | ip + iv, d0, 1 | 6/4 | 193 ± 15 | 619 ± 115 | 3.80 ± 1.01 | 57 |
| CPT-11 + XI | 20 + 25 | ip + iv, d0, 1 | 6/5 | 207 ± 13 | 601 ± 36 | 1.61 ± 0.57 | 33 |
| ADR + II | 4 + 25 | ip + iv, d0, 1 | 6/3 | 195 ± 19 | 573 ± 80 | 3.63 ± 1.09 | 50 |
| ADR + XI | 4 + 25 | ip + iv, d0, 1 | 6/3 | 180 ± 21 | 697 ± 64 | 4.60 ± 1.52 | 69 |
| ADR | 4 | ip, d0, 1 | 6/3 | 183 ± 13 | 667 ± 67 | 4.38 ± 1.38 | 64 |
| Control | Solvent | ip, d0, 1 | 10/8 | 154 ± 12 | 1022 ± 276 | 6.63 ± 1.62 | |

Notes:
d0: administration time for the first time;
dn: the 17$^{th}$ day after administration;
RTV: relative tumor volume;
Control group: n = 10;
Treatment group: n = 6;
ip: administration of intraperitoneal injection
iv: administration of intravenous injection
GCT is a control drug: Gemcitabine
ADR is a control drug: Adriamycin
CPT-11 is a control drug: Irinotecan It may be shown from the above tables that the compounds of the present invention not only have certain antitumor effects, and can also enhance the antitumor efficacy of the cytotoxic antitumor agents such as Gemcitabine, CPT-11, ADR and so on.

Although the present invention has been described in connection with the above embodiments, it should be understood that the present invention is not limited to such preferred embodiments and procedures set forth above. The embodiments and procedures were chosen and described in order to best explain the principles of the invention and its practical application, to thereby enable others skilled in the art to best utilize the invention. It will be apparent to those skilled in the art that various substitution, modifications and changes may be thereto without departing from the scope and spirit of the invention. Therefore, the intention is intended to cover all alternative constructions and equivalents falling within the spirit and scope of the invention as defined only by the appended claims and equivalents thereto.

What is claimed is:

1. A compound of formula (I) or a pharmaceutically acceptable salt or a hydrate thereof,

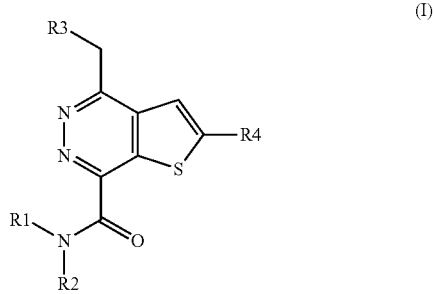

(I)

wherein, R1 and R2 are independently H or $C_{1-4}$ alkyl;

R3 is hexahydropyridinyl, tetrahydropyranyl, tetrahydrothiopyranyl, tetrahydropyrrolidinyl, tetrahydrofuranyl, tetrahydrothienyl, pyridinyl, α-pyranyl, γ-pyranyl, α-thiopyranyl, γ-thiopyranyl, pyrrolidinyl, furanyl, or thienyl and an optical isomer thereof;
R4 is a halophenyl monosubstituted or disubstituted at any position.

2. The compound or a pharmaceutically acceptable salt or a hydrate thereof according to claim 1, wherein R1=R2=H.

3. The compound or a pharmaceutically acceptable salt or a hydrate thereof according to claim 1, wherein R3 is hexahydropyridinyl, and an optical isomer thereof.

4. The compound or a pharmaceutically acceptable salt or a hydrate thereof according to claim 1, wherein R4 is a halophenyl monosubstituted

wherein X represents F, Cl, Br, I.

5. The compound or a pharmaceutically acceptable salt or a hydrate thereof according to claim 1, wherein the compounds of formula (I) is selected from:
  2-(4-fluorophenyl)-4-(3-piperidinemethyl)-thieno[2,3-d]pyridazinyl-7-formamide;
  2-(4-chlorophenyl)-4-(3-piperidinemethyl)-thieno[2,3-d]pyridazinyl-7-formamide;
  2-(4-bromophenyl)-4-(3-piperidinemethyl)-thieno[2,3-d]pyridazinyl-7-formamide;
  2-(4-fluorophenyl)-4-(3-tetrahydropyranmethyl)-thieno[2,3-d]pyridazinyl-7-formamide;
  2-(4-chlorophenyl)-4-(3-tetrahydropyranmethyl)-thieno[2,3-d]pyridazinyl-7-formamide;
  2-(4-bromophenyl)-4-(3-tetrahydropyranmethyl)-thieno[2,3-d]pyridazinyl-7-formamide;
  2-(4-fluorophenyl)-4-(3-tetrahydrothiapyranmethyl)-thieno[2,3-d]pyridazinyl-7-formamide;
  2-(4-chlorophenyl)-4-(3-tetrahydrothiapyranmethyl)-thieno[2,3-d]pyridazinyl-7-formamide;
  2-(4-bromophenyl)-4-(3-tetrahydrothiapyranmethyl)-thieno[2,3-d]pyridazinyl-7-formamide;
  2-(4-chlorophenyl)-4-(2-piperidinemethyl)-thieno[2,3-d]pyridazinyl-7-formamide;
  2-(4-chlorophenyl)-4-(4-piperidinemethyl)-thieno[2,3-d]pyridazinyl-7-formamide;
  2-(4-chlorophenyl)-4-(S-3-piperidinemethyl)-thieno[2,3-d] pyridazinyl-7-formamide;
  2-(4-chlorophenyl)-4-(R-3-piperidinemethyl)-thieno[2,3-d] pyridazinyl-7-formamide;
  2-(4-chlorophenyl)-4-(3-piperidinemethyl)-thieno [2,3-d]pyridazinyl-7-N-methyl-formamide;
  2-(4-chlorophenyl)-4-(3-piperidinemethyl)-thieno[2,3-d]pyridazinyl-7-N,N-dimethyl-7-formamide;
  2-(4-chlorophenyl)-4-(3-tetrahydrothiapyranmethyl)-thieno[2,3-d]pyridazinyl-7-N-methyl -formamide;
  2-(4-chlorophenyl)-4-(3-tetrahydrothiapyranmethyl)-thieno[2,3-d]pyridazinyl-7-N,N-dimethyl -7-formamide;
  2-(4-chlorophenyl)-4-(3-tetrahydropyranmethyl)-thieno [2,3-d]pyridazinyl-7-N-methyl-formamide;
  2-(4-chlorophenyl)-4-(3-tetrahydropyranmethyl)-thieno [2,3-d]pyridazinyl-7-N,N-dimethyl-7-formamide;
  2-(4-fluorophenyl)-4-(3-pyrrolidinemethyl)-thieno[2,3-d]pyridazinyl-7-formamide;
  2-(4-chlorophenyl)-4-(3-pyrrolidinemethyl)-thieno[2,3-d] pyridazinyl-7-formamide;
  2-(4-bromophenyl)-4-(3-pyrrolidinemethyl)-thieno[2,3-d] pyridazinyl-7-formamide;
  2-(4-fluorophenyl)-4-(3-tetrahydrofuranmethyl)-thieno [2,3-d]pyridazinyl-7-formamide;
  2-(4-chlorophenyl)-4-(3-tetrahydrofuranmethyl)-thieno [2,3-d]pyridazinyl-7-formamide;
  2-(4-bromophenyl)-4-(3-tetrahydrofuranmethyl)-thieno [2,3-d]pyridazinyl-7-formamide;
  2-(4-fluorophenyl)-4-(3-tetrahydrothiophenemethyl)-thieno[2,3-d]pyridazinyl-7-formamide;
  2-(4-chlorophenyl)-4-(3-tetrahydrothiophenemethyl)-thieno[2,3-d]pyridazinyl-7-formamide;
  2-(4-bromophenyl)-4-(3-tetrahydrothiophenemethyl)-thieno[2,3-d]pyridazinyl-7-formamide;
  2-(4-chlorophenyl)-4-(3-pyrrolidinemethyl)-thieno[2,3-d] pyridazinyl-7-formamide;
  2-(4-chlorophenyl)-4-(S-3-pyrrolidinemethyl)-thieno[2,3-d]pyridazinyl-7-formamide;
  2-(4-chlorophenyl)-4-(R-3-pyrrolidinemethyl)-thieno[2,3-d]pyridazinyl-7-formamide;
  2-(4-chlorophenyl)-4-(3-pyrrolidinemethyl)-thieno[2,3-d]pyridazinyl-7-N-methyl-formamide;
  2-(4-chlorophenyl)-4-(3-pyrrolidinemethyl)-thieno[2,3-d]pyridazinyl-7-N,N-dimethyl-formamide;
  2-(4-chlorophenyl)-4-(3-tetrahydrothiophenemethyl)-thieno[2,3-d]pyridazinyl-7-N-methyl-formamide;
  2-(4-chlorophenyl)-4-(3-tetrahydrothiophenemethyl)-thieno[2,3-d]pyridazinyl-7-N,N-dimethyl -formamide;
  2-(4-chlorophenyl)-4-(3-tetrahydrofuranmethyl)-thieno [2,3-d]pyridazinyl-7-N-methyl-formamide;
  2-(4-chlorophenyl)-4-(3-tetrahydrofuranmethyl)-thieno [2,3-d]pyridazinyl-7-N,N-dimethyl -formamide;
  2-(4-fluorophenyl)-4-(3-pyridinemethyl)-thieno[2,3-d] pyridazinyl-7-formamide;
  2-(4-chlorophenyl)-4-(3-pyridinemethyl)-thieno[2,3-d] pyridazinyl-7-formamide;
  2-(4-bromophenyl)-4-(3-pyridinemethyl)-thieno[2,3-d] pyridazinyl-7-formamide;
  2-(4-fluorophenyl)-4-(3-α-pyranmethyl)-thieno[2,3-d] pyridazinyl-7-formamide;
  2-(4-chlorophenyl)-4-(3-α-pyranmethyl)-thieno[2,3-d] pyridazinyl-7-formamide;
  2-(4-bromophenyl)-4-(3-α-pyranmethyl)-thieno[2,3-d] pyridazinyl-7-formamide;
  2-(4-fluorophenyl)-4-(3-α-thiopyranmethyl)-thieno[2,3-d] pyridazinyl-7-formamide;
  2-(4-chlorophenyl)-4-(3-α-thiopyranmethyl)-thieno[2,3-d] pyridazinyl-7-formamide;
  2-(4-bromophenyl)-4-(3-α-thiopyranmethyl)-thieno[2,3-d] pyridazinyl-7-formamide;
  2-(4-chlorophenyl)-4-(2-pyridinemethyl)-thieno[2,3-d] pyridazinyl-7-formamide;
  2-(4-chlorophenyl)-4-(4-pyridinemethyl)-thieno[2,3-d] pyridazinyl-7-formamide;
  2-(4-chlorophenyl)-4-(3-pyridinemethyl)-thieno[2,3-d] pyridazinyl-7-N-methyl formamide;
  2-(4-chlorophenyl)-4-(3-pyridinemethyl)-thieno[2,3-d] pyridazinyl-7-N,N-dimethyl formamide;
  2-(4-chlorophenyl)-4-(3-thiopyranylmethyl)-thieno[2,3-d]pyridazinyl-7-N-methyl formamide;
  2-(4-chlorophenyl)-4-(3-thiopyranylmethyl)-thieno[2,3-d]pyridazinyl-7-N,N-dimethyl formamide;
  2-(4-chlorophenyl)-4-(3-pyranmethyl)-thieno[2,3-d]pyridazinyl-7-N-methyl formamide;
  2-(4-chlorophenyl)-4-(3-pyranmethyl)-thieno[2,3-d]pyridazinyl-7-N,N-dimethyl formamide;

2-(4-fluorophenyl)-4-(3-pyrrolemethyl)-thieno[2,3-d]
pyridazinyl-7-formamide;
2-(4-chlorophenyl)-4-(3-pyrrolemethyl)-thieno[2,3-d]
pyridazinyl-7-formamide;
2-(4-bromophenyl)-4-(3-pyrrolemethyl)-thieno[2,3-d]
pyridazinyl-7-formamide;
2-(4-fluorophenyl)-4-(3-furanmethyl)-thieno[2,3-d]
pyridazinyl-7-formamide;
2-(4-chlorophenyl)-4-(3-furanmethyl)-thieno[2,3-d]
pyridazinyl-7-formamide;
2-(4-bromophenyl)-4-(3-furanmethyl)-thieno[2,3-d]
pyridazinyl-7-formamide;
2-(4-fluorophenyl)-4-(3-thiaphenemethyl)-thieno[2,3-d]
pyridazinyl-7-formamide;
2-(4-chlorophenyl)-4-(3-thiaphenemethyl)-thieno[2,3-d]
pyridazinyl-7-formamide;
2-(4-bromophenyl)-4-(3-thiaphenemethyl)-thieno[2,3-d]
pyridazinyl-7-formamide;
2-(4-chlorophenyl)-4-(2-pyrrolemethyl)-thieno[2,3-d]
pyridazinyl-7-formamide;
2-(4-chlorophenyl)-4-(3-pyrrolemethyl)-thieno[2,3-d]pyridazinyl-7-N-methyl formamide;
2-(4-chlorophenyl)-4-(3-pyrrolemethyl)-thieno[2,3-d]pyridazinyl-7-N,N-dimethyl formamide;
2-(4-chlorophenyl)-4-(3-thiaphenemethyl)-thieno[2,3-d]
pyridazinyl-7-N-methyl formamide;
2-(4-chlorophenyl)-4-(3-thiaphenemethyl)-thieno[2,3-d]
pyridazinyl-7-N,N-dimethyl formamide;
2-(4-chlorophenyl)-4-(3-furanmethyl)-thieno[2,3-d]pyridazinyl-7-N-methyl formamide;
2-(4-chlorophenyl)-4-(3-furanmethyl)-thieno[2,3-d]pyridazinyl-7-N,N-dimethyl formamide;
2-(3,5-dichlorophenyl)-4-(3-piperidinemethyl)-thieno[2,3-d]pyridazinyl-7-formamide.

6. A pharmaceutical composition comprising a therapeutically effective amount of compound of formula (I) of any one of the claims 1, 2, 3, 4 and 5 or a pharmaceutically acceptable salt or a hydrate thereof, and a pharmaceutically acceptable carrier.

7. A method for preparing the compound of formula (I) or a pharmaceutically acceptable salt or a hydrate thereof of any one of claims 1, 2, 3, 4 and 5,

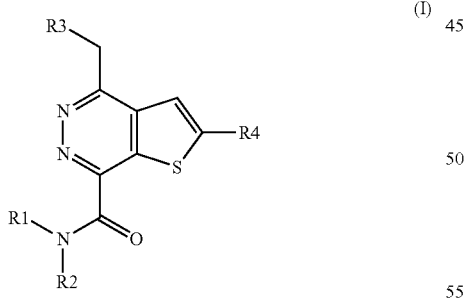

wherein R1 and R2 are independently H or $C_{1-4}$ alkyl respectively; R3 is hexahydropyridinyl, tetrahydropyranyl, tetrahydrothiopyranyl, tetrahydropyrrolidinyl, tetrahydrofuranyl, or tetrahydrothienyl, and an optical isomer thereof; R4 is a halophenyl monosubstituted or disubstituted at any position;

the method comprising following steps:

1) a compound of formula A is treated with dialkyl oxalate diethyl oxalate in the presence of alkali lithium diisopropylamide and an organic solvent tetrahydrofuran to produce a compound Y;

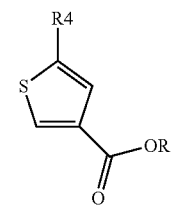

2) the compound Y is reacted with hydrazine $H_2NNH_2$ in alcoholic solvent to produce a compound of formula B;

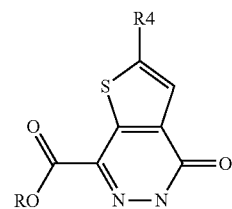

3) the compound of formula B is treated with phosphorus oxychloride for an acylation reaction to produce a compound of formula C;

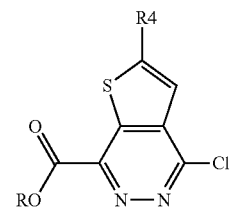

4) the compound of formula C is reacted with the compound $R_3CH_2$ containing a Boc protecting group at a reaction temperature of 80~90° C. in presence of catalysts $PdCl_2$ (dppf) and solvents phosphates /1,4-dioxane for overnight, to produce a compound of formula D,

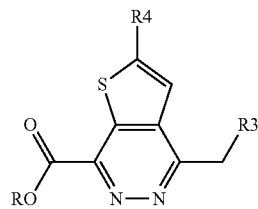

5) the compounds of formula D and HNR1R2 are ammonolyzed in a sealed container using conventional methods with reaction solvents of 1,4-dioxane, under heating at temperature of 80° C. for overnight, then a Boc protecting group on R3 is removed under acidic conditions to obtain the acid salts of formula (I), and adjust pH with alkali to produce the compound of formula (I);

wherein R is a $C_{1-4}$ alkyl, and wherein the definition of R1,R2,R3 and R4 of the steps 1), 2), 3), 4) and 5) is the same as that of the compound of formula (I).

* * * * *